US012788225B2

(12) United States Patent
Chiang et al.

(10) Patent No.: US 12,788,225 B2
(45) Date of Patent: Nov. 10, 2026

(54) ENDOSCOPIC SAME AXIS-MAINTAINING SYSTEM, COAXIAL OPTICAL SYSTEM, AND ENDOSCOPIC IMAGING SYSTEM AND APPLICATION THEREOF

(71) Applicant: ANHUI DENDRITE MEDICAL EQUIPMENT CO., LTD, Hefei (CN)

(72) Inventors: Li-Yang Chiang, Shanghai (CN); Xianjie Weng, Shanghai (CN)

(73) Assignee: ANHUI DENDRITE MEDICAL EQUIPMENT CO., LTD., Hefei (CN)

( * ) Notice: Subject to any disclaimer, the term of this patent is extended or adjusted under 35 U.S.C. 154(b) by 241 days.

(21) Appl. No.: 18/710,802

(22) PCT Filed: Nov. 29, 2023

(86) PCT No.: PCT/CN2023/134941
§ 371 (c)(1),
(2) Date: May 16, 2024

(87) PCT Pub. No.: WO2025/060247
PCT Pub. Date: Mar. 27, 2025

(65) Prior Publication Data
US 2025/0311916 A1 Oct. 9, 2025

(30) Foreign Application Priority Data
Sep. 22, 2023 (CN) ......................... 202311227346.0

(51) Int. Cl.
*A61B 1/00* (2006.01)
*A61B 1/002* (2006.01)
*G02B 23/24* (2006.01)

(52) U.S. Cl.
CPC .......... *A61B 1/002* (2013.01); *G02B 23/2476* (2013.01)

(58) Field of Classification Search
CPC . A61B 1/002; A61B 1/00163; A61B 1/00177; A61B 1/00179; A61B 1/00135;
(Continued)

(56) References Cited

U.S. PATENT DOCUMENTS

2014/0200406 A1* 7/2014 Bennett .................. A61B 1/127 600/109
2022/0007926 A1* 1/2022 Ruiz Corrales .......... A61B 1/07
2023/0273422 A1* 8/2023 Duckett, III ....... G02B 13/0095 359/642

FOREIGN PATENT DOCUMENTS

DE 19509885 A1 * 9/1995 ......... G02B 23/2415
JP 2017074267 A * 4/2017
WO WO-2018135192 A1 * 7/2018 ............. G02B 13/00

* cited by examiner

*Primary Examiner* — Anhtuan T Nguyen
*Assistant Examiner* — Rynae E Boler
(74) *Attorney, Agent, or Firm* — Bayramoglu Law Offices LLC

(57) ABSTRACT

The present invention provides an endoscopic same axis-maintaining system, a coaxial optical system, and an endoscopic imaging system and application thereof. The endoscopic same axis-maintaining system includes: a transfer lens sheath, a connecting member, and an imaging lens sheath sequentially arranged along a same optical axis from an image side. The same optical axis of the transfer lens sheath and the imaging lens sheath is formed with the transfer lens sheath and the imaging lens sheath axially abutting against, in opposite directions, a radial outer wall and a radial inner wall of the connecting member, respectively. The transfer lens sheath is sleeved outwards with an inner lens sheath and an outer lens sheath sequentially, coaxially, and radially, and the outer lens sheath is axially separated from the inner lens sheath. At least part of the outer lens sheath axially extends beyond an imaging lens sheath object-side end, and the outer lens sheath is radially
(Continued)

separated from or connected to the connecting member. This application improves the overall low stability of the endoscopic same axis-maintaining system due to actions such as accidental impacts or shaking during operation, avoiding a decrease in clarity of a biological body image during transmission.

14 Claims, 12 Drawing Sheets

(58) Field of Classification Search
CPC .............. G02B 23/2476; G02B 23/243; G02B 13/0095; G02B 13/2466
See application file for complete search history.

ENDOSCOPIC SAME AXIS-MAINTAINING SYSTEM, COAXIAL OPTICAL SYSTEM, AND ENDOSCOPIC IMAGING SYSTEM AND APPLICATION THEREOF

This application claims priority to Chinese Patent Application No. 202311227346.0, filed with the China National Intellectual Property Administration on Sep. 22, 2023 and entitled "ENDOSCOPIC SAME AXIS-MAINTAINING SYSTEM, COAXIAL OPTICAL SYSTEM, AND ENDOSCOPIC IMAGING SYSTEM AND APPLICATION THEREOF", which is incorporated herein by reference in its entirety.

FIELD OF TECHNOLOGY

The present invention relates to the field of optical technologies, and in particular to, an endoscopic same axis-maintaining system, a coaxial optical system, and an endoscopic imaging system and application thereof.

BACKGROUND

An endoscope is a device that examines or treats tissues in the human body using a head probe and optical lenses based on the operation principles of optical imaging and probe technology. With a light source and lenses introduced into body cavities or tissues, microscopic structures or pathological tissues inside the body can be observed. The optical imaging principle of the endoscope means that light of a light source behind the human body enters into the body, and is reflected by an inner wall of an endoscope head and then guided by optical fibers to observation equipment. The optical lens of the endoscope focuses the light, thereby forming an enlarged image for the doctor's observation. Therefore, the quality of the optical imaging directly affects the use effect of the endoscope.

The optical imaging of the endoscope mainly relies on the optical system arranged therein. The optical system is formed by an object lens, a relay lens set, and an eyepiece arranged sequentially from the front end at which a biological tissue is located to the rear end. The object lens is used to collect information of the biological tissue for imaging, the relay lens set is used to transmit the image, and the eyepiece is used to enlarge the image for clinical observation by the doctor. The foundation of optical imaging is the biological tissue information collected by the object lens. Therefore, the collection of biological tissue information is an indispensable and crucial part. To ensure the optical axes of the relay lens set and the object lens are the same axis, the relative positions of the lens included in the relay lens set and the object lens are strictly required during mounting.

However, it is difficult to maintain the overall stability of the lens sheath in the prior art due to actions such as accidental impacts or shaking during operation. This results in likely misalignment between the axes of a rod lens set and the object lens set, thus affecting the clarity of image being transmitted by the rod lens set.

In view of this, it is necessary to improve the optical system in the prior art, so as to resolve the foregoing problem.

SUMMARY

An objective of the present invention is to disclose an endoscopic same axis-maintaining system, a coaxial optical system, and an endoscopic imaging system and application thereof, so as to resolve the problem in the prior art that the overall low stability of the optical system due to actions such as accidental impacts or shaking during operation decreases the clarity of image during transmission.

To achieve the foregoing objective, according to a first aspect, the present invention provides an endoscopic same axis-maintaining system, including: a transfer lens sheath, a connecting member, and an imaging lens sheath sequentially arranged along a same optical axis from an image side.

The same optical axis of the transfer lens sheath and the imaging lens sheath is formed with the transfer lens sheath and the imaging lens sheath axially abutting against, in opposite directions, a radial outer wall and a radial inner wall of the connecting member, respectively.

The transfer lens sheath is sleeved outwards with an inner lens sheath and an outer lens sheath sequentially, coaxially, and radially, and the outer lens sheath is axially separated from the inner lens sheath.

At least part of the outer lens sheath axially extends beyond an imaging lens sheath object-side end, the outer lens sheath is radially separated from or connected to the connecting member, and a gap is present between the outer lens sheath and the inner lens sheath for the outer lens sheath to be axially separated from the inner lens sheath.

As further improvement of the present invention, the connecting member protrudes outwards radially to form an outer abutting portion for the transfer lens sheath to axially abut against, and the connecting member is concaved inwards radially to form a maintaining portion of the connecting member for the imaging lens sheath to axially abut against and partially extend into.

The same optical axis of the transfer lens sheath and the imaging lens sheath is formed with the transfer lens sheath and the imaging lens sheath axially abutting against, in opposite directions, the outer abutting portion and the maintaining portion, respectively.

As further improvement of the present invention, the outer lens sheath is radially separated from at least part of the outer abutting portion.

The outer lens sheath being radially separated from the at least part of the outer abutting portion is achieved through clearance or interference fitting between the outer lens sheath and the at least part of the outer abutting portion, such that the outer lens sheath is axially separated from the outer abutting portion.

As further improvement of the present invention, the outer lens sheath is radially connected to at least part of the outer abutting portion.

The outer lens sheath is fixedly connected to the at least part of the outer abutting portion, such that the outer lens sheath drives the connecting member to be axially separated from the transfer lens sheath.

As further improvement of the present invention, the transfer lens sheath is in clearance or interference fitting with the inner lens sheath.

As further improvement of the present invention, a first abutting surface formed with the transfer lens sheath axially abutting against the outer abutting portion and a second abutting surface formed with the imaging lens sheath axially abutting against the maintaining portion are axially apart from each other or on radial planes along the same optical axis.

According to a second aspect, the present invention further provides a coaxial optical system, including: a transfer mechanism, a connecting member, and an imaging mechanism sequentially arranged along a same optical axis from an image side.

The same optical axis of the transfer mechanism and the imaging mechanism is formed with a transfer lens sheath included by the transfer mechanism and an imaging lens sheath included by the imaging mechanism axially abutting against, in opposite directions, a radial outer wall and a radial inner wall of the connecting member, respectively; The transfer lens sheath is sleeved outwards with an inner lens sheath and an outer lens sheath sequentially, coaxially, and radially, and the outer lens sheath is axially separated from the inner lens sheath.

At least part of the outer lens sheath axially extends beyond an imaging lens sheath object-side end, and the outer lens sheath is radially separated from or connected to the connecting member.

As further improvement of the present invention, a gap is present between the outer lens sheath and the inner lens sheath for the outer lens sheath to be axially separated from the inner lens sheath.

As further improvement of the present invention, the connecting member protrudes outwards radially to form an outer abutting portion for the transfer lens sheath to axially abut against, and the connecting member is concaved inwards radially to form a maintaining portion of the connecting member for the imaging lens sheath to axially abut against and partially extend into.

The same optical axis of the transfer lens sheath and the imaging lens sheath is formed with the transfer lens sheath and the imaging lens sheath axially abutting against, in opposite directions, the outer abutting portion and the maintaining portion, respectively.

As further improvement of the present invention, the outer lens sheath is radially separated from at least part of the outer abutting portion.

The outer lens sheath being radially separated from the at least part of the outer abutting portion is achieved through clearance or interference fitting between the outer lens sheath and the at least part of the outer abutting portion, such that the outer lens sheath is axially separated from the outer abutting portion.

As further improvement of the present invention, the outer lens sheath is radially connected to at least part of the outer abutting portion.

The outer lens sheath is fixedly connected to the at least part of the outer abutting portion, such that the outer lens sheath drives the connecting member to be axially separated from the transfer lens sheath.

As further improvement of the present invention, a first abutting surface formed with the transfer lens sheath axially abutting against the outer abutting portion and a second abutting surface formed with the imaging lens sheath axially abutting against the maintaining portion are axially apart from each other or on radial planes along the same optical axis.

As further improvement of the present invention, the transfer mechanism includes three or more transfer lens sets, in an odder quantity, disposed at the transfer lens sheath at intervals of the same optical axis, and a plurality of first isolating rings axially abutted between adjacent two of the transfer lens sets.

The transfer lens set is symmetrically formed by two rod-shaped lens sets.

As further improvement of the present invention, the outer abutting portion forms a limiting end at least partially and axially extending into the transfer lens sheath, and the limiting end axially abuts against the rod-shaped lens set in a transfer lens sheath object-side end.

As further improvement of the present invention, the limiting end is circumferentially provided with at least one annular groove, and the annular groove is embedded with a filling layer preventing the transfer lens sheath from being axially separated from the connecting member.

As further improvement of the present invention, the filling layer is an adhesive medium or a sealing medium.

As further improvement of the present invention, the connecting member is constructed with a connecting channel arranged axially, the imaging lens sheath is partially accommodated in the connecting channel, and the connecting channel protrudes inwards radially to form the maintaining portion for the imaging lens sheath to axially abut against.

As further improvement of the present invention, the transfer lens sheath is in clearance or interference fitting with the inner lens sheath.

As further improvement of the present invention, the imaging mechanism includes a first lens set with a positive focal power, a second lens set with a positive focal power, a third lens set with a positive focal power, and a fourth lens set with a positive focal power that are sequentially arranged from an object side along the same optical axis.

The first lens set includes a second lens with a plane facing the object side, the second lens set includes a fourth lens with a convex surface facing the object side and a fifth lens with a convex surface facing the image side that fit with each other, the third lens set includes a sixth lens with a convex surface facing the object side and a concave surface facing the image side, and the fourth lens set includes a seventh lens with a concave surface facing the object side and a convex surface facing the image side and an eighth lens with a convex surface facing the object side and a concave surface facing the image side.

A combined focal length $f_1$ of the first lens set and a conjugate distance T satisfy $$0.15 \leq \frac{f_1}{T} \leq 0.18,$$

a combined focal length $f_4$ of the fourth lens set and the combined focal length $f_1$ of the first lens set satisfy $$1.8 \leq f_4/f_1 \leq 2.2,$$

and a focal length $f_{41}$ of the seventh lens and a focal length $f_{42}$ of the eighth lens satisfy $$-1 \leq f_{42}/f_{41} \leq -0.8.$$

As further improvement of the present invention, the first lens set further includes a third lens disposed on an image side of the second lens along the same optical axis; and a surface of the third lens facing the image side forms a convex surface.

As further improvement of the present invention, the first lens set further includes a first lens disposed on an object side of the second lens along the same optical axis and having a plane facing the object side.

As further improvement of the present invention, the outer lens sheath axially extends beyond the imaging lens sheath object-side end to form a protective end, and the first lens is disposed at the protective end along the same optical axis.

As further improvement of the present invention, the coaxial optical system further includes: a lens base configured at an outer lens sheath image-side end and an adapter base detachably connected to the lens base.

As further improvement of the present invention, the lens base is constructed with an accommodating channel accommodating at least part of the transfer lens sheath, and the accommodating channel forms radially inwards a step recess for a transfer lens sheath image-side end to axially abut against.

As further improvement of the present invention, the inner lens sheath axially penetrates through the adapter base and extends into the lens base, so as to abut against the step recess formed by the lens base, and the inner lens sheath is axially abutted between the lens base and the outer abutting portion.

According to a third aspect, the present invention further provides an endoscopic imaging system, including a lens base with a dichroscope, a light source, and the coaxial optical system according to any one of descriptions in the second aspect. The lens base included by the coaxial optical system receives light incident from the light source onto the dichroscope, and after reflection by the dichroscope, the coaxial optical system captures the light reflected again by an object under test, and the reflected light penetrates through the dichroscope to be captured by the endoscopic imaging system.

According to a fourth aspect, the present invention further provides application of an endoscopic imaging system, where the endoscopic imaging system described according to the third aspect is used to optically image a biological body tissue.

Compared with the prior art, the present invention has the following beneficial effects: The transfer lens sheath and the imaging lens sheath are mounted fixedly using the connecting member, enabling the axis of the transfer lens sheath and the axis of the imaging lens sheath to overlap and to be on the same optical axis, thus achieving the same optical axis of the transfer lens sheath and the imaging lens sheath, so as to ensure the clarity of an image plane, during transmission, generated by performing optical imaging on a biological body tissue. In addition, the outer lens sheath and the inner lens sheath are assembled tightly and radially, preventing the outer lens sheath from vibrating with respect to the inner lens sheath during disassembly or assembly, or operation, thus improving the overall stability of the endoscopic same axis-maintaining system. This prevents actions by an operator such as accidental impacts on the outer lens sheath or shaking during operation from causing likely misalignment between the axes of the transfer lens sheath and the imaging lens sheath, thus ensuring the transfer mechanism and the imaging mechanism can maintain the same optical axis all the time.

DESCRIPTION OF THE EMBODIMENTS

Figure 1:
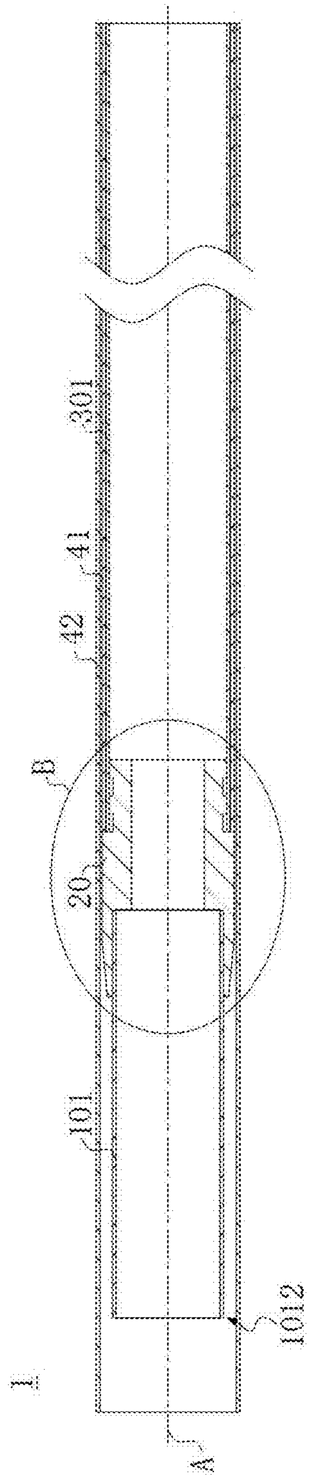
FIG. 1 is a cross-sectional view of an endoscopic same axis-maintaining system according to the present invention.

The following describes the present invention in detail with reference to implementations shown in the accompanying drawings, but it should be noted that these implementations do not impose limitations on the present invention. Functional, methodological, or structural equivalent transformations or substitutions made by persons of ordinary skill in the art according to these implementations all fall into the protection scope of the present invention. It should be noted that in the following embodiments, the term “optical axis” refers to the optical axis A in FIG. 1. The term “axially” means being parallel to the optical axis A. At an angle of view shown in FIGS. 1 to 3, as shown in FIG. 3, an object side is in a direction in which an object W under test is located, and an image side is in a direction opposite to the object W under test. In addition, for ease of description, the lens included by a coaxial optical system is defined as an optical element, and in a practical application scenario (for example, an endoscope described below is used to observe a biological body), before a biological body imaging system is used to image the biological body, an end of the biological body imaging system close to the object side is immersed in normal saline to form a layer of physiological saline at the end. Further, for ease of description in the following embodiments, in this application, the normal saline can be also defined as an optical element. The object W under test includes a living creature or a detached biological tissue.

“MTF” in the “MTF graph” of the present invention stands for modulation transfer function. In the transfer function, the abscissa represents spatial frequency in the unit of cycles per millimeter, and the ordinate represents the image contrast of the corresponding frequency.

Refer to specific implementations for an endoscopic same axis-maintaining system, a coaxial optical system, and an endoscopic imaging system and application thereof disclosed in FIGS. 1 to 21.

As shown in FIGS. 1 to 4, the endoscopic same axis-maintaining system 1 may be mounted on an optical inspection device for observing a biological body (which includes a living creature or a detached biological tissue). The endoscopic same axis-maintaining system 1 is used to accommodate a rod lens set and an object lens set and achieve the same optical axis between the rod lens set and the object lens set, and can prevent actions by an operator (for example, medical personnel or scientific researcher) such as accidental impacts or shaking during operation from causing misalignment between the axes of the rod lens set and the object lens. This can ensure image clarity when the rod lens set transmits an image plane, which is generated by using the object lens set to perform optical imaging on the biological body tissue, thus allowing for observation on the biological body image by the operator. Specifically, an optical inspection device may be, for example, an endoscope, which is a type of tool for minimally invasive medical procedures in the human body. The endoscope is designed to enter the human body through a natural cavity or a small surgical incision in the body and guided to be inserted into the biological tissue that needs to be examined, so as to obtain the corresponding images of the biological body tissue for observation by the medical personnel. In addition, the applicant points out that the endoscope is specifically used as an example for exemplary description in the following specification. Certainly, the optical inspection device may alternatively be a device used for crack detection in the industrial sector. This is not limited in this embodiment, but does not limit the protection scope of this application.

As shown in FIGS. 1 to 4, in this implementation, the endoscopic same axis-maintaining system 1 includes a transfer lens sheath 301, a connecting member 20, and an imaging lens sheath 101 sequentially arranged along a same optical axis from an image side. The same optical axis of the transfer lens sheath 301 and the imaging lens sheath 101 is formed with the transfer lens sheath 301 and the imaging lens sheath 101 axially abutting against, in opposite directions, a radial outer wall and a radial inner wall of the connecting member 20, respectively. The transfer lens sheath 301, the connecting member 20, and the imaging lens sheath 101 are sequentially arranged along the same optical axis from the image side. The connecting member 20 is disposed at a transfer lens sheath object-side end 3012, the imaging lens sheath 101 is disposed at a connecting member object-side end 24, and the transfer lens sheath 301 and the imaging lens sheath 101, in opposite directions, axially abut against the connecting member 20. Specifically, the transfer lens sheath 301 axially abuts against the radial outer wall of the connecting member 20, and the connecting member 20 is mounted at the transfer lens sheath object-side end 3012. The imaging lens sheath 101 axially abuts against the radial inner wall of the connecting member 20 and is mounted at the connecting member object-side end 24. The transfer lens sheath 301 and the imaging lens sheath 101 are fixedly mounted using the connecting member 20, enabling the axis of the transfer lens sheath 301 and the axis of the imaging lens sheath 101 to overlap and to be on the same optical axis A, achieving the same optical axis of the transfer lens sheath 301 and the imaging lens sheath 101, thus ensuring image clarity during transmission.

The transfer lens sheath 301 is sleeved outwards with an inner lens sheath 41 and an outer lens sheath 42 sequentially, coaxially, and radially, and the outer lens sheath 42 is axially separated from the inner lens sheath 41. The outer lens sheath 42 is disassembled or assembled with respect to the inner lens sheath 41. In addition, the outer lens sheath 42 and the inner lens sheath 41 are assembled tightly and radially, preventing the outer lens sheath 42 from vibrating with respect to the inner lens sheath 41 during disassembly or assembly, or operation, thus improving the overall stability of the endoscopic same axis-maintaining system 1. This prevents actions by an operator such as accidental impacts on the outer lens sheath 42 or shaking during operation from causing likely misalignment between the axes of the transfer lens sheath 301 and the imaging lens sheath 101, thus ensuring the transfer lens sheath 301 and the imaging lens sheath 101 can maintain the same optical axis.

At least part of the outer lens sheath 42 axially extends beyond an imaging lens sheath object-side end 1012. The outer side of the transfer lens sheath 301 is coaxially sleeved with the inner lens sheath 41, and the outer side of the inner lens sheath 41 is coaxially sleeved with the outer lens sheath 42. The outer lens sheath 42 sleeves the outer sides of the connecting member 20 and the imaging lens sheath 101 and at least partially and axially extends beyond the imaging lens sheath object-side end 1012. The outer lens sheath 42 can protect the transfer lens sheath 301, the connecting member 20, and the imaging lens sheath 101, preventing the transfer lens sheath 301, the connecting member 20, and the imaging lens sheath 101 from directly coming into contact with the outside.

The outer lens sheath 42 is radially separated from or connected to the connecting member 20. The outer lens sheath 42 being radially separated from the connecting member 20 is conducive to disassembling or assembling the outer lens sheath 42 with respect to the connecting member 20, or the outer lens sheath 42 being radially connected to the connecting member 20 is conducive for the outer lens sheath 42 to synchronously drive the connecting member 20 to be disassembled or assembled with respect to the transfer lens sheath 301.

Figure 4:
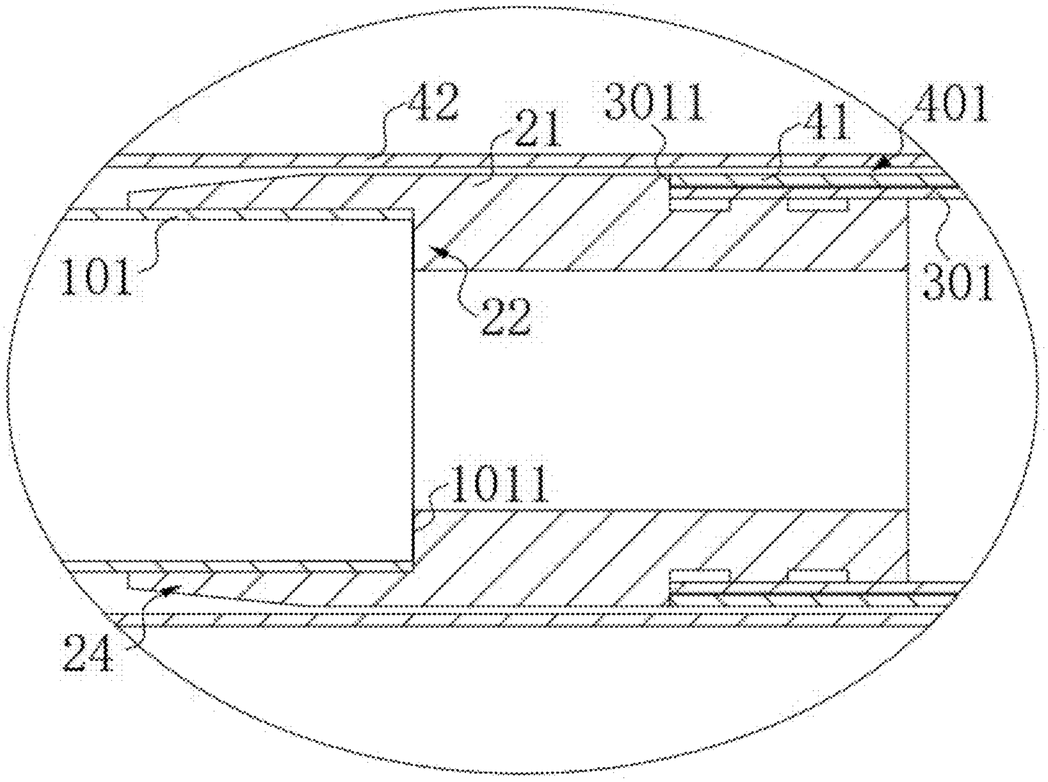
FIG. 4 is a locally enlarged view at a circle B in FIG. 1.

As shown in FIG. 4, a gap 401 is present between the outer lens sheath 42 and the inner lens sheath 41 for the outer lens sheath 42 to be axially separated from the inner lens sheath 41. As the outer lens sheath 42 and the inner lens sheath 41 are assembled radially and tightly and the gap 401 is present between the outer lens sheath 42 and the inner lens sheath 41, the overall stability of the endoscopic same axis-maintaining system 1 is improved and the outer lens sheath 42 can be radially separated from the inner lens sheath 41. This is conducive to disassembling or assembling the outer lens sheath 42 with respect to the inner lens sheath 41, preventing the outer lens sheath 42 from vibrating with respect to the inner lens sheath 41 during disassembly or assembly, or operation.

The transfer lens sheath 301 is in clearance or interference fitting with the inner lens sheath 41. The transfer lens sheath 301 and the inner lens sheath 41 are assembled radially and tightly, and a gap (not shown) is present between the outer peripheral wall of the transfer lens sheath 301 and the inner peripheral wall of the inner lens sheath 41. Alternatively, the outer peripheral wall of the transfer lens sheath 301 is in radial interference fitting with the inner peripheral wall of the inner lens sheath 41 (not shown), or the outer peripheral wall of the transfer lens sheath 301 fits with the inner peripheral wall of the inner lens sheath 41 as shown in FIG. 4 as long as the transfer lens sheath 301 and the inner lens sheath 41 are assembled radially and tightly and the inner lens sheath 41 can be axially separated from the transfer lens sheath 301 for disassembly or assembly.

As shown in FIGS. 1 and 4, the connecting member 20 protrudes outwards radially to form an outer abutting portion 21 for the transfer lens sheath 301 to axially abut against, and the connecting member 20 is concaved inwards radially to form a maintaining portion 22 of the connecting member 20 for the imaging lens sheath 101 to axially abut against and partially extend into. The same optical axis of the transfer lens sheath 301 and the imaging lens sheath 101 is formed with the transfer lens sheath 301 and the imaging lens sheath 101 axially abutting against, in opposite directions, the outer abutting portion 21 and the maintaining portion 22, respectively. The connecting member 20 protrudes outwards radially to form the outer abutting portion 21, and the transfer lens sheath 301 axially abuts against the outer abutting portion 21. The connecting member 20 is concaved inwards radially to form the maintaining portion 22, and the imaging lens sheath 101 axially abuts against and partially extends into the maintaining portion 22. The transfer lens sheath 301 and the imaging lens sheath 101, in opposite directions, axially abut against the outer abutting portion 21 and the maintaining portion 22, respectively. The connecting member 20 is disposed at the transfer lens sheath object-side end 3012 via the outer abutting portion 21, the imaging lens sheath 101 is disposed at the connecting member object-side end 24 via the maintaining portion 22, and the transfer lens sheath 301 and the imaging lens sheath 101 are fixedly mounted via the connecting member 20 by respectively using the outer abutting portion 21 and the maintaining portion 22. This enables the axis of the transfer lens sheath 301 and the axis of the imaging lens sheath 101 to overlap and to be on the same optical axis A, achieving the same optical axis of the transfer lens sheath 301 and the imaging lens sheath 101, thus ensuring image clarity during transmission.

Figure 5:
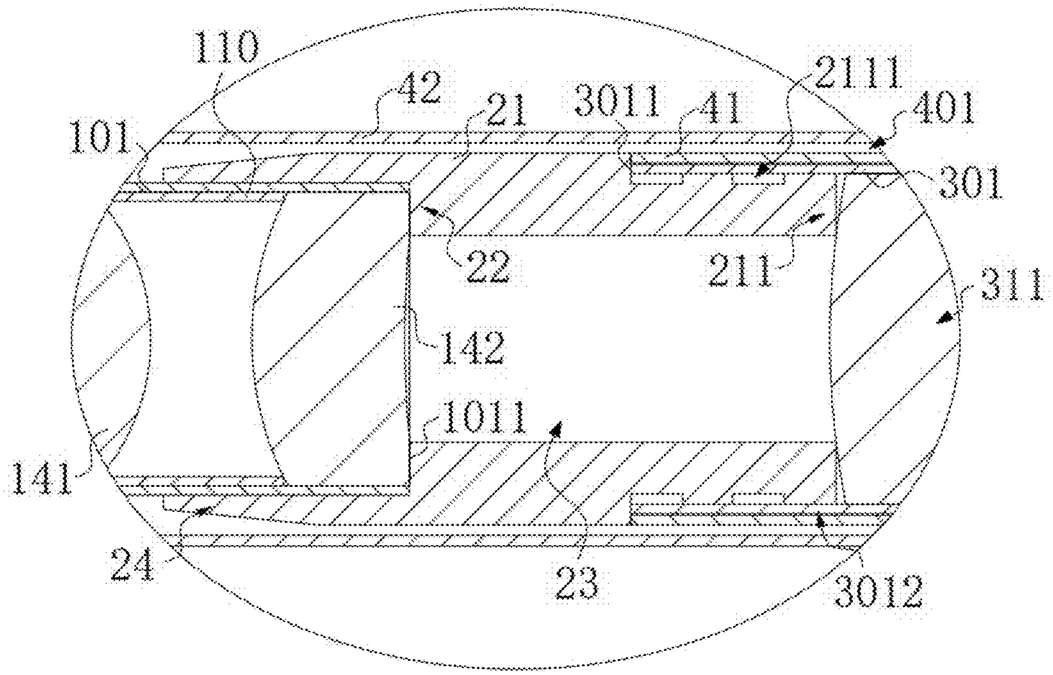
FIG. 5 is a locally enlarged view at a circle C in FIG. 2.

In some embodiments, the outer lens sheath 42 is radially separated from at least part of the outer abutting portion 21. When the connecting member object-side end 24 inclines inwards to be cone-shaped in a direction of the optical axis A, the outer lens sheath 42 is radially separated from at least part of the outer peripheral wall of the outer abutting portion 21, as shown in FIG. 5. In some embodiments, the outer lens sheath 42 may alternatively be radially separated from the whole outer peripheral wall of the outer abutting portion 21 (not shown). The outer lens sheath 42 being radially separated from the at least part of the outer abutting portion 21 is achieved through clearance or interference fitting between the outer lens sheath 42 and the at least part of the outer abutting portion 21, such that the outer lens sheath 42 is axially separated from the outer abutting portion 21. The outer lens sheath 42 may be in clearance fitting with at least part of the outer peripheral wall of the outer abutting portion 21, as shown in FIG. 4. In some embodiments, the outer lens sheath 42 may alternatively be in interference fitting with the at least part of the outer peripheral wall of the outer abutting portion 21 (not shown). In this embodiment, the outer lens sheath 42 is preferably in clearance fitting with at least part of the outer peripheral wall of the outer abutting portion 21. As the outer lens sheath 42 is in clearance or interference fitting with at least part of the outer peripheral wall of the outer abutting portion 21, the outer lens sheath 42 may also incline inwards in the direction of the optical axis A to form the cone-shaped connecting member object-side end 24. The outer lens sheath 42 is assembled outside the connecting member 20 from the connecting member object-side end 24 in the direction of the image side. The cone-shaped connecting member object-side end 24 facilitates interference fitting between the outer lens sheath 42 and the connecting member 20 because the cone-shaped connecting member object-side end 24 reduces the compression distance between the outer lens sheath 42 and the connecting member 20 during interference fitting. This is conducive to disassembling and assembling the outer lens sheath 42, and when the outer lens sheath 42 is disassembled or assembled, a fitting surface between the outer lens sheath 42 and the connecting member 20 is less likely to be scratched. It should be noted, the assembly method for the interference fitting between the outer lens sheath 42 and the connecting member 20 may be but is not limited to a pressing method, a temperature difference method, and a hydraulic method.

In some embodiments, the outer lens sheath 42 is radially connected to at least part of the outer abutting portion 21. When the connecting member object-side end 24 inclines inwards to be cone-shaped in a direction of the optical axis A, the outer lens sheath 42 is radially connected to at least part of the outer peripheral wall of the outer abutting portion 21, as shown in FIG. 5. In some embodiments, the outer lens sheath 42 may alternatively be radially separated from the whole outer peripheral wall of the outer abutting portion 21 (not shown). The outer lens sheath 42 is fixedly connected to the at least part of the outer abutting portion 21, such that the outer lens sheath 42 drives the connecting member 20 to be axially separated from the transfer lens sheath 301. The outer lens sheath 42 may be fixedly connected to at least part of the outer peripheral wall of the outer abutting portion 21 via laser welding or an adhesive medium, or in another manner. This enables the outer lens sheath 42 to drive the connecting member 20 to be axially separated from the transfer lens sheath 301 for disassembly or assembly. When the outer lens sheath 42 is fixedly connected to the at least part of the outer peripheral wall of the outer abutting portion 21, the outer diameter of the inner lens sheath 41 is preferably smaller than the outer diameter of the connecting member 20, avoiding scratch between the outer lens sheath 42 and the inner lens sheath 41 during disassembly or assembly.

Based on the endoscopic same axis-maintaining system 1 disclosed in the foregoing embodiment, this embodiment further discloses a coaxial optical system 100.

Figure 2:
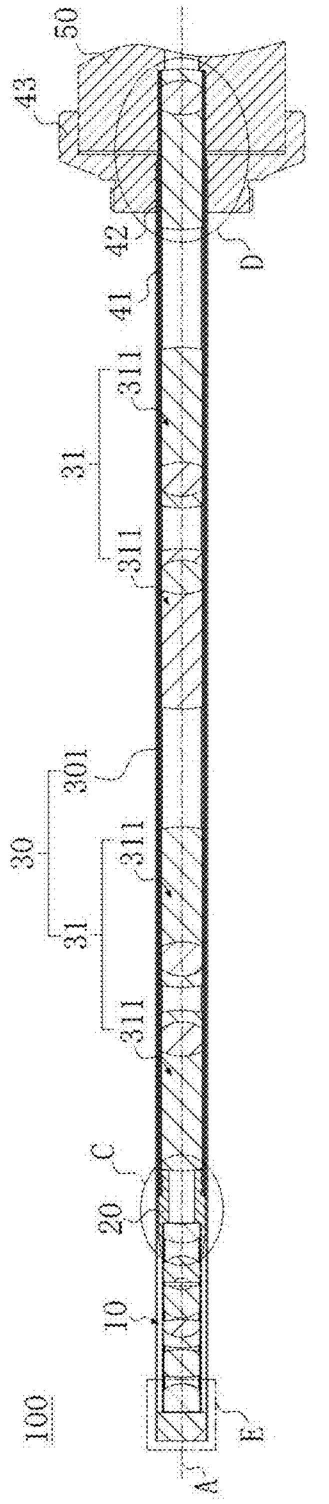
FIG. 2 is a cross-sectional view of a coaxial optical system according to the present invention.
Figure 3:
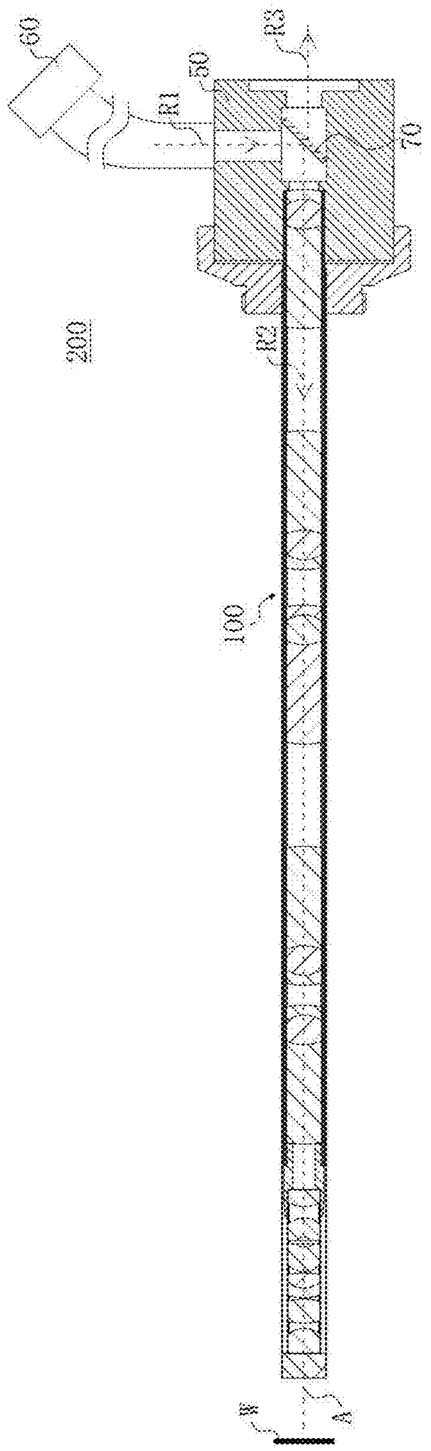
FIG. 3 is a cross-sectional diagram of an endoscopic imaging system including a coaxial optical system according to the present invention.
Figure 6:
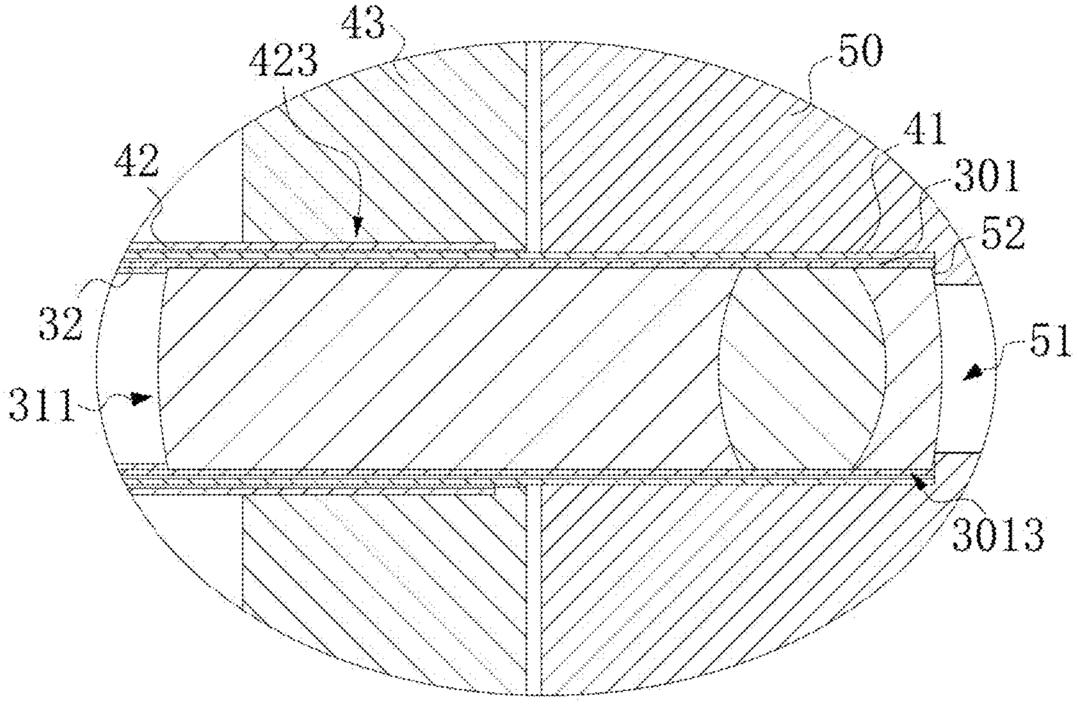
FIG. 6 is a locally enlarged view at a circle D in FIG. 2.

As shown in FIGS. 2, 5, and 6, the coaxial optical system 100 may be mounted on an optical inspection device for observing a biological body (which includes a living creature or a detached biological tissue), specifically forming an insertion portion of the optical inspection device and enabling the transfer mechanism 30 and the imaging mechanism 10 to have the same optical axis. The insertion portion is inserted into the body of the creature under test for optical imaging on the creature body tissue, and can prevent actions by an operator (for example, medical personnel or scientific researcher) such as accidental impacts or shaking during operation from causing misalignment between the axes of the transfer mechanism 30 and the imaging mechanism 10. This can ensure image clarity when the transfer mechanism 30 transmits an image plane, which is generated by using the imaging mechanism 10 to perform optical imaging on the biological body tissue, thus allowing for observation on the biological body image by the operator. Specifically, an optical inspection device may be, for example, an endoscope, which is a type of tool for minimally invasive medical procedures in the human body. The endoscope is designed to enter the human body through a natural cavity or a small surgical incision in the body and guided to be inserted into the biological tissue that needs to be examined, so as to obtain the corresponding images of the biological body tissue for observation by the medical personnel. In addition, the applicant points out that the endoscope is specifically used as an example for exemplary description in the following specification. Certainly, the optical inspection device may alternatively be a device used for crack detection in the industrial sector. This is not limited in this embodiment, but does not limit the protection scope of this application.

The coaxial optical system 100 includes a transfer mechanism 30, a connecting member 20, and an imaging mechanism 10 sequentially arranged along a same optical axis from an image side. The same optical axis of the transfer mechanism 30 and the imaging mechanism 10 is formed with a transfer lens sheath 301 included by the transfer mechanism 30 and an imaging lens sheath 101 included by the imaging mechanism 10 axially abutting against, in opposite directions, a radial outer wall and a radial inner wall of the connecting member 20, respectively. The transfer mechanism 30, the connecting member 20, and the imaging mechanism 10 are sequentially arranged along a same optical axis from an image side. The connecting member 20 is disposed at a transfer lens sheath object-side end 3012, the imaging lens sheath 101 is disposed at a connecting member object-side end 24, and the transfer mechanism 30 and the imaging mechanism 10, in opposite directions, axially abut against the connecting member 20. Specifically, the transfer lens sheath 301 and the imaging lens sheath 101, in opposite directions, axially abut against the connecting member 20. The transfer lens sheath 301 axially abuts against the radial outer wall of the connecting member 20, and the connecting member 20 is mounted at the transfer lens sheath object-side end 3012. The imaging lens sheath 101 axially abuts against the radial inner wall of the connecting member 20 and is mounted at the connecting member object-side end 24. The transfer lens sheath 301 and the imaging lens sheath 101 are fixedly mounted using the connecting member 20, enabling the axis of the transfer lens sheath 301 and the axis of the imaging lens sheath 101 to overlap and to be on the same optical axis A, achieving the same optical axis of the transfer mechanism 30 and the imaging mechanism 10, thus ensuring image clarity when the transfer mechanism 30 transmits an image plane, which is generated by using the imaging mechanism 10 to perform optical imaging on the biological body tissue.

The transfer lens sheath 301 is sleeved outwards with an inner lens sheath 41 and an outer lens sheath 42 sequentially, coaxially, and radially, and the outer lens sheath 42 is axially separated from the inner lens sheath 41. The outer lens sheath 42 is disassembled or assembled with respect to the inner lens sheath 41. In addition, the outer lens sheath 42 and the inner lens sheath 41 are assembled tightly and radially, preventing the outer lens sheath 42 from vibrating with respect to the inner lens sheath 41 during disassembly or assembly, or operation, thus improving the overall stability of the coaxial optical system 100. This prevents actions by an operator such as accidental impacts on the outer lens sheath 42 or shaking during operation from causing likely misalignment between the axes of the transfer lens sheath 301 and the imaging lens sheath 101, thus ensuring the transfer lens sheath 301 and the imaging lens sheath 101 can maintain the same optical axis.

At least part of the outer lens sheath 42 axially extends beyond the imaging lens sheath object-side end 1012. The outer side of the transfer lens sheath 301 is coaxially sleeved with the inner lens sheath 41, and the outer side of the inner lens sheath 41 is coaxially sleeved with the outer lens sheath 42. The outer lens sheath 42 sleeves the outer sides of the connecting member 20 and the imaging lens sheath 101 and at least partially and axially extends beyond the imaging lens sheath object-side end 1012. The outer lens sheath 42 can protect the transfer lens sheath 301, the connecting member 20, and the imaging lens sheath 101, preventing the transfer lens sheath 301, the connecting member 20, and the imaging lens sheath 101 from directly coming into contact with the outside.

The outer lens sheath 42 is radially separated from or connected to the connecting member 20. The outer lens sheath 42 being radially separated from the connecting member 20 is conducive to disassembling or assembling the outer lens sheath 42 with respect to the connecting member 20, or the outer lens sheath 42 being radially connected to the connecting member 20 is conducive for the outer lens sheath 42 to synchronously drive the connecting member 20 to be disassembled or assembled with respect to the transfer lens sheath 301.

As shown in FIGS. 2 and 5, further, a gap 401 is present between the outer lens sheath 42 and the inner lens sheath 41 for the outer lens sheath 42 to be axially separated from the inner lens sheath 41. As the outer lens sheath 42 and the inner lens sheath 41 are assembled radially and tightly and the gap 401 is present between the outer lens sheath 42 and the inner lens sheath 41, the overall stability of the coaxial optical system 100 is improved and the outer lens sheath 42 can be radially separated from the inner lens sheath 41. This is conducive to disassembling or assembling the outer lens sheath 42 with respect to the inner lens sheath 41, preventing the outer lens sheath 42 from vibrating with respect to the inner lens sheath 41 during disassembly or assembly, or operation.

The transfer lens sheath 301 is in clearance or interference fitting with the inner lens sheath 41. The transfer lens sheath 301 and the inner lens sheath 41 are assembled radially and tightly, and a gap (not shown) is present between the outer peripheral wall of the transfer lens sheath 301 and the inner peripheral wall of the inner lens sheath 41. Alternatively, the outer peripheral wall of the transfer lens sheath 301 is in radial interference fitting with the inner peripheral wall of the inner lens sheath 41 (not shown), or the outer peripheral wall of the transfer lens sheath 301 fits with the inner peripheral wall of the inner lens sheath 41 as shown in FIG. 4 as long as the transfer lens sheath 301 and the inner lens sheath 41 are assembled radially and tightly and the inner lens sheath 41 can be axially separated from the transfer lens sheath 301 for disassembly or assembly.

As shown in FIGS. 2 and 5, specifically, the connecting member 20 protrudes outwards radially to form an outer abutting portion 21 for the transfer lens sheath 301 to axially abut against, and the connecting member 20 is concaved inwards radially to form a maintaining portion 22 of the connecting member 20 for the imaging lens sheath 101 to axially abut against and partially extend into. The same optical axis of the transfer lens sheath 301 and the imaging lens sheath 101 is formed with the transfer lens sheath 301 and the imaging lens sheath 101 axially abutting against, in opposite directions, the outer abutting portion 21 and the maintaining portion 22, respectively. The connecting member 20 protrudes outwards radially to form the outer abutting portion 21, and the transfer lens sheath 301 axially abuts against the outer abutting portion 21. The connecting member 20 is concaved inwards radially to form the maintaining portion 22, and the imaging lens sheath 101 axially abuts against and partially extends into the maintaining portion 22. The transfer lens sheath 301 and the imaging lens sheath 101, in opposite directions, axially abut against the outer abutting portion 21 and the maintaining portion 22, respectively. The connecting member 20 is disposed at the transfer lens sheath object-side end 3012 via the outer abutting portion 21, the imaging lens sheath 101 is disposed at the connecting member object-side end 24 via the maintaining portion 22, and the transfer lens sheath 301 and the imaging lens sheath 101 are fixedly mounted via the connecting member 20 by using the outer abutting portion 21 and the maintaining portion 22. This enables the axis of the transfer lens sheath 301 and the axis of the imaging lens sheath 101 to overlap and to be on the same optical axis A, achieving the same optical axis of the transfer mechanism 30 and the imaging mechanism 10, thus ensuring image clarity when the transfer mechanism 30 transmits an image plane, which is generated by using the imaging mechanism 10 to perform optical imaging on the biological body tissue. As shown in FIG. 5, in some embodiments, the outer lens sheath 42 is radially separated from at least part of the outer abutting portion 21. When the connecting member object-side end 24 inclines inwards to be cone-shaped in a direction of the optical axis A, the outer lens sheath 42 is radially separated from at least part of the outer peripheral wall of the outer abutting portion 21, as shown in FIG. 5. In some embodiments, the outer lens sheath 42 may alternatively be radially separated from the whole outer peripheral wall of the outer abutting portion 21 (not shown). The outer lens sheath 42 being radially separated from the at least part of the outer abutting portion 21 is achieved through clearance or interference fitting between the outer lens sheath 42 and the at least part of the outer abutting portion 21, such that the outer lens sheath 42 is axially separated from the outer abutting portion 21. The outer lens sheath 42 may be in clearance fitting with at least part of the outer peripheral wall of the outer abutting portion 21, as shown in FIG. 5. In some embodiments, the outer lens sheath 42 may alternatively be in interference fitting with the at least part of the outer peripheral wall of the outer abutting portion 21 (not shown). In this embodiment, the outer lens sheath 42 is preferably in clearance fitting with at least part of the outer peripheral wall of the outer abutting portion 21. As the outer lens sheath 42 is in clearance or interference fitting with at least part of the outer peripheral wall of the outer abutting portion 21, the outer lens sheath 42 may also incline inwards in the direction of the optical axis A to form the cone-shaped connecting member object-side end 24. The outer lens sheath 42 is assembled outside the connecting member 20 from the connecting member object-side end 24 in the direction of the image side. The cone-shaped connecting member object-side end 24 facilitates interference fitting between the outer lens sheath 42 and the connecting member 20 because the cone-shaped connecting member object-side end 24 reduces the compression distance between the outer lens sheath 42 and the connecting member 20 during interference fitting. This is conducive to disassembling and assembling the outer lens sheath 42, and when the outer lens sheath 42 is disassembled or assembled, a fitting surface between the outer lens sheath 42 and the connecting member 20 is less likely to be scratched. It should be noted, the assembly method for the interference fitting between the outer lens sheath 42 and the connecting member 20 may be but is not limited to a pressing method, a temperature difference method, and a hydraulic method.

As shown in FIG. 5, in some embodiments, the outer lens sheath 42 is radially connected to at least part of the outer abutting portion 21. When the connecting member object-side end 24 inclines inwards to be cone-shaped in a direction of the optical axis A, the outer lens sheath 42 is radially connected to at least part of the outer peripheral wall of the outer abutting portion 21, as shown in FIG. 5. In some embodiments, the outer lens sheath 42 may alternatively be radially separated from the whole outer peripheral wall of the outer abutting portion 21 (not shown). The outer lens sheath 42 is fixedly connected to the at least part of the outer abutting portion 21, such that the outer lens sheath 42 drives the connecting member 20 to be axially separated from the transfer lens sheath 301. The outer lens sheath 42 may be fixedly connected to at least part of the outer peripheral wall of the outer abutting portion 21 via laser welding or an adhesive medium, or in another manner. This enables the outer lens sheath 42 to drive the connecting member 20 to be axially separated from the transfer lens sheath 301 for disassembly or assembly. When the outer lens sheath 42 is fixedly connected to the at least part of the outer peripheral wall of the outer abutting portion 21, the outer diameter of the inner lens sheath 41 is preferably smaller than the outer diameter of the connecting member 20, avoiding scratch between the outer lens sheath 42 and the inner lens sheath 41 during disassembly or assembly.

As shown in FIG. 5, a first abutting surface 3011 formed with the transfer lens sheath 301 axially abutting against the outer abutting portion 21 and a second abutting surface 1011 formed with the imaging lens sheath 101 axially abutting against the maintaining portion 22 are axially apart from each other or on radial planes along the same optical axis. The first abutting surface 3011 and the second abutting surface 1011 are axially apart from each other, and the second abutting surface 1011 is located in a direction of the first abutting surface 3011 close to the object side, as shown in FIG. 5. In some embodiments, the second abutting surface 1011 may alternatively be in a direction of the first abutting surface 3011 close to the image side (not shown) or the first abutting surface 3011 and the second abutting surface 1011 may be on radial planes along the same optical axis A (not shown) as long as the same optical axis of the transfer mechanism 30 and the imaging mechanism 10 can be achieved, to ensure clarity of the image plane, which is generated by the imaging mechanism 10, during transmission by the transfer mechanism 30.

As shown in FIGS. 5 and 6, the transfer mechanism 30 includes three or more transfer lens sets 31, in an odder quantity, disposed at the transfer lens sheath 301 at intervals of the same optical axis, and a plurality of first isolating rings 32 axially abutted between adjacent two of the transfer lens sets 31. The transfer lens set 31 is symmetrically formed by two rod-shaped lens sets 311. The quantity of the transfer lens sets 31 is an odd number equal to or more than three, so as to output an erect real image. The first isolating ring 32 can fix the position of the rod-shaped lens set 311, to fix the axial distance between the plurality of rod-shaped lens sets 311, avoiding displacement of the rod-shaped lens set 311 in the transfer lens sheath 301 and enabling the plurality of rod-shaped lens sets 311 to be along the same optical axis.

As shown in FIG. 5, the outer abutting portion 21 forms a limiting end 211 at least partially and axially extending into the transfer lens sheath 301, and the limiting end 211 axially abuts against the rod-shaped lens set 311 in a transfer lens sheath object-side end 3012. The transfer lens sheath 301 axially abuts against the outer abutting portion 21 and the outer abutting portion 21 forms the limiting end 211 at least partially and axially extending into the transfer lens sheath 301. The connecting member 20 is axially mounted at the transfer lens sheath object-side end 3012 via the limiting end 211 and axially abuts against the rod-shaped lens sets 311 in the transfer lens sheath object-side end 3012 via the limiting end 211, to fit with the first isolating ring 32, so as to fix the positions of the plurality of rod-shaped lens sets 311 in the transfer lens sheath 301 and fix the axial distance between the plurality of rod-shaped lens sets 311 in the transfer lens sheath 301.

As shown in FIG. 5, in this embodiment, preferably, the limiting end 211 is circumferentially provided with at least one annular groove 2111, and the annular groove 2111 is embedded with a filling layer preventing the transfer lens sheath 301 from being axially separated from the connecting member 20. The filling layer is an adhesive medium or a sealing medium. The adhesive medium or the sealing medium is embedded in the annular groove 2111 to mount the connecting member 20 at the transfer lens sheath object-side end 3012, preventing the transfer lens sheath 301 from being axially separated from the connecting member 20 due to external force, thus improving the stability of assembling the transfer lens sheath 301 with the connecting member 20. It should be noted that the adhesive medium is preferably an optical glue, and the sealing medium is preferably a sealing ring such as an O-shaped sealing ring.

As shown in FIG. 5, specifically, the connecting member 20 is constructed with a connecting channel 23 arranged axially, the imaging lens sheath 101 is partially accommodated in the connecting channel 23, and the connecting channel 23 protrudes inwards radially to form a maintaining portion 22 for the imaging lens sheath 101 to axially abut against. The connecting member 20 is constructed with a connecting channel 23 accommodating at least part of the imaging lens sheath 101, and the connecting channel 23 protrudes inwards radially to form the maintaining portion 22 for the imaging lens sheath 101 to abut against, such that the imaging lens sheath 101 is mounted in the connecting channel 23. The imaging lens sheath 101 may be fixedly connected to the connecting member object-side end 24 via laser welding or an adhesive medium, or in another manner.

Figure 9:
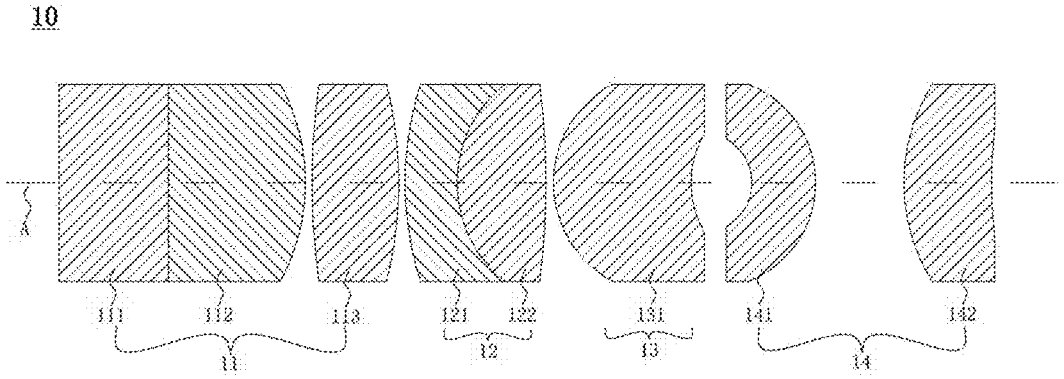
FIG. 9 is a structural cross-sectional view of an imaging mechanism including an optical axis A in FIGS. 2 and 3, where a first lens, a second lens, and a third lens set form a first lens set.

As shown in FIG. 9, the imaging mechanism 10 includes a first lens set 11 with a positive focal power, a second lens set 12 with a positive focal power, a third lens set 13 with a positive focal power, and a fourth lens set 14 with a positive focal power that are sequentially arranged from an object side along the same optical axis (that is, the optical axis A shown in FIG. 9). The first lens set 11 is used for setting parameter data (for example, numerical aperture, field of view) of the imaging mechanism 10, determining the basic performance of the imaging mechanism 10. The second lens set 12 is disposed between the first lens set 11 and the third lens set 13 along the same optical axis to correct aberrations, which are mainly spherical aberration, comatic aberration, and chromatic aberration. The third lens set 13 is configured to achieve finite conjugate-distance imaging and also to correct field curvature. The fourth lens set 14 is configured to achieve telecentric imaging in the image space, thus ensuring the imaging effect of the imaging mechanism 10. Additionally, it can further guarantee clarity of images during long-distance transmission through telecentric imaging in the image space, reducing the optical loss during long-distance transmission.

It should be noted that the telecentric imaging in the image space is to enable a chief ray in each off-axis field of view in the image space to be parallel to the optical axis (or approximately parallel to the optical axis), and non-telecentric imaging in the image space is to enable the chief ray in each off-axis field of view not to be parallel to the optical axis. The chief rays are typically located at the center of the defocused spot corresponding to the field of view in the image space. When the chief ray is on the image plane, the defocused spot is minimized, and when the chief ray is behind the image plane, the defocused spot gradually becomes large. For a telecentric system, behind the image plane, the chief ray is not changed in height and angle, and for a non-telecentric system, the chief ray increases in height and remains unchanged in angle. For the receiving system behind, the telecentric system requires a smaller diameter and deflection angle of the receiving system than the non-telecentric system. It can be therefore seen that telecentric imaging in the image space can keep image clarity unchanged during long-distance transmission.

The first lens set 11 includes a second lens 112 disposed along the optical axis A with a plane facing the object side. A surface of the second lens 112 facing the image side forms a convex surface. Light rays reflected by the surface of the biological body sequentially pass through the plane and the convex surface respectively formed on the object side and the image side of the second lens 112 to be gathered, effectively avoiding the problem that the reflected light rays cannot pass through the second lens set 12 due to the large reflection angle, thus reducing light loss. The surface of the second lens 112 facing the object side may be a convex surface or a plane, and is preferably a plane, so as to prevent or reduce the residual attachment such as liquid on the surface (that is, the surface of the second lens 112 facing the object side) when the imaging mechanism 10 is carried on the optical inspection device for use.

The first lens set 11 further includes a third lens 113 disposed on the image side of the second lens 112 along the same optical axis. The surface of the third lens 113 facing the image side forms a convex surface. The light rays reflected by the surface of the object are refracted by the second lens 112 to form refracted light rays. The third lens 113 is disposed on the image side of the second lens 112 to perform secondary gathering on the light rays refracted by the second lens 112, further avoiding the problem that the refracted light rays are unable to pass through the second lens set 12 due to a large refraction angle (which is equivalent to the refraction angle formed by the optical axis A), thus reducing the light loss. The surface of the third lens 113 facing the object side forms a convex surface or a plane. When the surface of the third lens 113 facing the object side forms a convex surface, second gathering is performed on the refracted light rays through the convex surface (that is, the surface of the third lens 113 facing the object side), and third gathering is performed on the refracted light rays through the convex surface of the third lens 113 facing the image side, still further avoiding the problem that the refracted light rays are unable to pass through the second lens set 12 due to a large refraction angle, thus reducing the light loss. When the surface of the third lens 113 facing the object side forms a plane, the plane (that is, a plane of the third lens 113 facing the object side) does not gather the refracted light rays, which undergo second gathering only by the convex surface of the third lens 113 facing the image side. This avoids the problem that the refracted light rays are unable to pass through the second lens set 12 due to a large refraction angle, thus reducing light loss. The surface of the third lens 113 facing the object side may be a convex surface or a plane as long as the third lens 113 can gather the light rays refracted by the second lens 112.

The first lens set 11 further includes a first lens 111 disposed on an object side of the second lens 112 along the same optical axis and having a plane facing the object side. The first lens 111 is disposed on the object side of the second lens 112, that is, at a position in the imaging mechanism 10 closest to the object side, to shield optical elements such as the second lens 112, the third lens 113, and the second lens set 12, thus avoiding scratch on the surface of the second lens 112 facing the object side. In addition, the first lens 111 is arranged as a flat lens, avoiding the change in optical path when the reflected light rays pass through the first lens 111, where due to such change, some or all of the refracted light rays cannot pass through the second lens 112, thus reducing light loss, that is, reducing the interference of the first lens 111 with the optical path of the reflected light rays. In a practical application scenario, the first lens 111 may also be normal saline.

It should be noted that the second lens 112 alone may form a first lens set 11, the second lens 112 and the third lens 113 are combined to form the first lens set 11, the first lens 111 and the second lens 112 are combined to form the first lens set 11, or the first lens 111, the second lens 112, and the third lens 113 are combined to form the first lens set 11. The combination manner of the first lens set 11 is not specifically limited in this embodiment. Any one of the foregoing cases stands as long as the first lens set 11 can gather the light rays reflected by the surface of the biological body surface, such that the parameter data of the imaging mechanism 10 is set, such as the numerical aperture, field of view. In addition, preferably, if the first lens 111, the second lens 112, and the third lens 113 are combined to form the first lens set 11, the first lens 111 is a flat lens, the second lens 112 is a plano-convex lens, and the third lens 113 is a double-convex lens.

The second lens 112 and the third lens 113 included by the first lens set 11, the second lens set 12, the third lens set 13, and the fourth lens set 14 are disposed in the imaging lens sheath 101 along the same optical axis. A plurality of second isolating rings 110 are abutted axially between the first lens set 11, the second lens set 12, the third lens set 13, and the fourth lens set 14, such that the second isolating rings 110 fix the first lens set 11, the second lens set 12, the third lens set 13, and the fourth lens set 14 and the axial distance.

Figure 7:
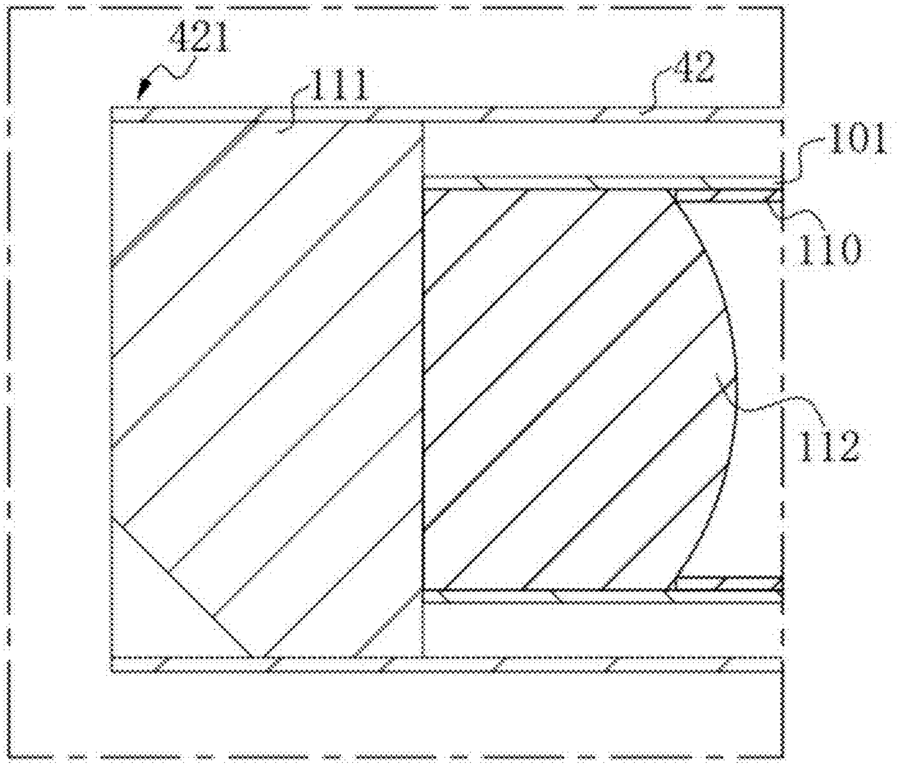
FIG. 7 is a locally enlarged view at a dashed box E in FIG. 2.
Figure 8:
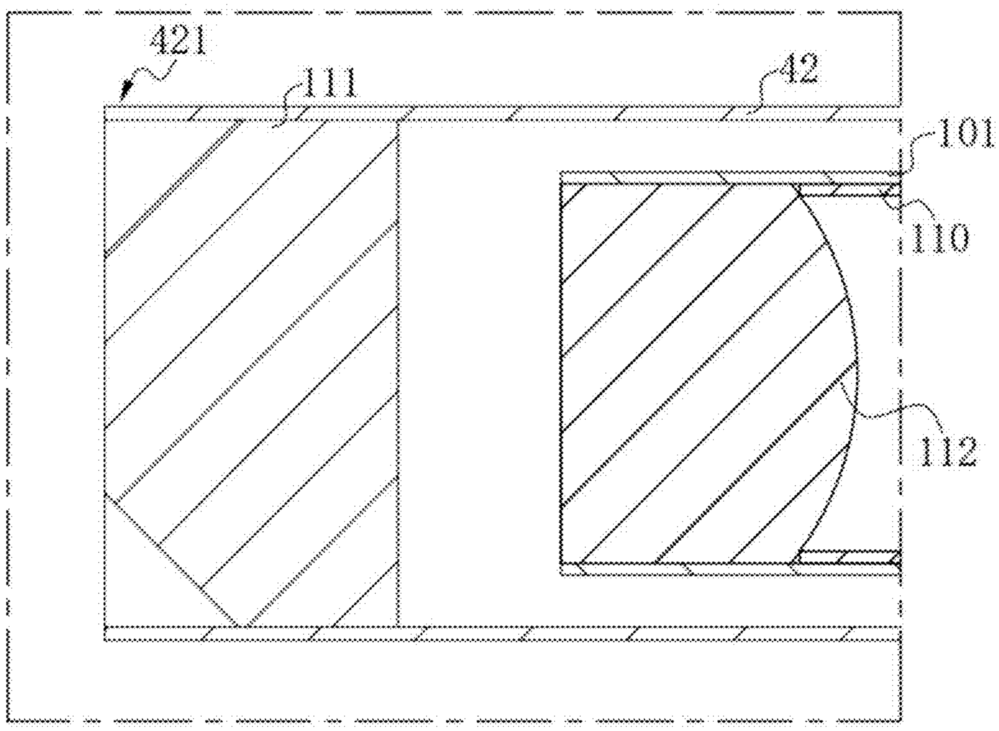
FIG. 8 is a schematic diagram of a first lens and a second lens according to a variable embodiment.

The outer lens sheath 42 axially extends beyond the imaging lens sheath object-side end 1012 to form a protective end 421, and the first lens 111 included in the first lens set 11 is disposed at the protective end 421 along the same optical axis. It should be noted that for the arrangement manner of the first lens 111 and the second lens 112, the first lens 111 may fit with the second lens 112 (as shown in FIG. 7), or the first lens 111 may be axially apart from the second lens 112 (as shown in FIG. 8). In this implementation, preferably, the first lens 111 fits with the second lens 112 (as shown in FIG. 7), the surfaces of the first lens 111 on the object side and image side are both planes. The fitting arrangement means that the surface of the first lens 111 facing the image side and the surface of the second lens 112 facing the object side fit into one surface, so as to eliminate refraction losses by two surfaces (that is, the surface of the first lens 111 facing the image side and the surface of the second lens 112 facing the object side) and prevent total refraction in the gap. This further is conducive to providing a dust-proof function for optical elements such as the second lens set 12 or the third lens set 13, thus avoiding scratch on the surface of the second lens 112 facing the object side. Optionally, the gap between the first lens 111 and the second lens 112 may be vacuumed, to reduce the interference of air with refracted light.

The second lens set 12 includes a fourth lens 121 with a convex surface facing the object side and a fifth lens 122 with a convex surface facing the image side that fit with each other along the same optical axis A. The fourth lens 121 has a convex surface facing the object side and a concave surface facing the image side, and the surface of the fifth lens 122 facing the image side and the surface facing the object side are both convex surfaces. The refracted light rays passing through the first lens set 11 sequentially pass through the fourth lens 121 and the fifth lens 122. The fourth lens 121 diverges the refracted light rays passing through the first lens set 11, and the fifth lens 122 gathers the refracted light rays passing through the fourth lens 121, so as to correct spherical aberration, comatic aberration, and chromatic aberration.

The arrangement manner of the fourth lens 121 and the fifth lens 122 may be fitting as described above. That is, the surface of the fourth lens 121 facing the image side fits with the surface of the fifth lens 122 facing the object side, to form the second lens set 12 which has a positive focal power, so as to eliminate refraction losses by two surfaces (that is, the surface of the fourth lens 121 facing the image side and the surface of the fifth lens 122 facing the object side) and prevent total refraction in the gap. This is also conducive to mounting the fourth lens 121 and the fifth lens 122. Certainly, as described above, the gap between the fourth lens 121 and the fifth lens 122 may also be vacuumed to reduce the interference of the gap with refracted light.

The third lens set 13 includes a sixth lens 131 arranged along the same optical axis A. The surface of the sixth lens 131 facing the object side forms a convex surface, and the surface of the sixth lens 131 facing the image side forms a concave surface, such that the convex surface gathers the refracted light rays from the second lens set 12 (or the first lens set 11), and the concave surface diverges refracted light rays from the convex surface, thus achieving finite conjugate-distance imaging and correcting field curvature (that is, curvature of the image field).

The fourth lens set 14 includes a seventh lens 141 and an eighth lens 142 sequentially arranged from the object side along the same optical axis A. The surface of the seventh lens 141 facing the object side forms a concave surface, and the surface facing the image side forms a convex surface. The surface of the eighth lens 142 facing the object side forms a convex surface and the surface facing the image side forms a concave surface. The concave surface of the seventh lens 141 diverges the refracted light rays passing through the third lens set 13, and the convex surface of the seventh lens 141 gathers the refracted light rays. The convex surface of the eighth lens 142 gathers the refracted light rays passing through the seventh lens 141, and the concave surface of the eighth lens 142 diverges the refracted light rays, so as to achieve telecentric imaging in the image space.

It should be noted that as shown in FIG. 9, in this application, the first lens set 11, the second lens set 12, the third lens set 13, and the fourth lens set 14 may form the imaging mechanism 10. The parameter data (for example, numerical aperture, field of view) of the imaging mechanism 10 is controlled using the first lens set 11, to determine the basic performance of the imaging mechanism 10. The second lens set 12 is used to correct aberrations, which are mainly spherical aberration, comatic aberration, and chromatic aberration. The third lens set 13 is used to achieve finite conjugate-distance imaging and correct field curvature. The fourth lens set 14 is used to achieve telecentric imaging in the image space, thus ensuring the imaging effect of the imaging mechanism 10 and further guaranteeing clarity of images during long-distance transmission through telecentric imaging in the image space, so as to reduce the optical loss during long-distance transmission.

In this implementation, each optical element satisfies the following condition: A combined focal length $f_1$ of the first lens set 11 and the conjugate distance T (that is, the conjugate distance T of the imaging mechanism 10) satisfy $$0.15 \leq f_1/T \leq 0.18.$$

The combined focal length $f_1$ of the first lens set 11 and the combined focal length $f_2$ of the second lens set 12 satisfy $$7 \leq f_2/f_1 \leq 11.5.$$

The combined focal length $f_2$ of the second lens set 12 and the combined focal length $f_3$ of the third lens set 13 satisfy $$2.2 \leq f_2/f_3 \leq 4.5.$$

The combined focal length $f_4$ of the fourth lens set 14 and the combined focal length $f_1$ of the first lens set 11 satisfy $$1.8 \leq f_4/f_1 \leq 2.2.$$

The focal length $f_{41}$ of the seventh lens 141 and the focal length $f_{42}$ of the eighth lens 142 satisfy $$-1 \leq f_{42}/f_{41} \leq -0.8.$$

The curvature radius $r_3$ corresponding to the surface of the second lens 112 facing the image side and the focal length $f_{12}$ of the second lens 112 satisfy $$-0.91 \leq r_3/f_{12} \leq -0.81.$$

The curvature radius $r_9$ corresponding to the convex surface of the sixth lens 131 facing the object side and the combined focal length $f_3$ of the third lens set 13 satisfy $$0.15 \leq r_9/f_3 \leq 0.35.$$

The curvature radius $r_{12}$ corresponding to the convex surface of the seventh lens 141 facing the image side and the curvature radius $r_{13}$ corresponding to the convex surface of the eighth lens 142 facing the object side satisfy $$-0.7 \leq r_{12}/r_{13} \leq -0.5.$$

The central thickness $D_9$ of the sixth lens 131 and the conjugate distance T satisfy $$0.13 \leq D_9/T.$$

If the surface of the third lens 113 facing the object side forms a convex surface, the curvature radius $r_4$ corresponding to the surface of the third lens 113 facing the object side, the operating distance H of the imaging mechanism 10, and an air gap $H_1$ between the second lens 112 and the third lens 113 satisfy $$4.75 \leq r_4/(H+H_1) \leq 15.9.$$

The air gap $H_1$ refers to a distance corresponding to a gap between a central position of the second lens 112 and the central position of the third lens 113, and the operating distance HH refers to a distance corresponding to a gap between a central position of a surface of the second lens 112 facing the object side and the biological body.

Embodiment 1

The lens structure of an imaging mechanism 10 in Embodiment 1 is shown in FIG. 9. For the method shown in the figure, reference is made to the foregoing description, and repeated description is omitted herein.

The imaging mechanism 10 in Embodiment 1 is formed by sequentially arranging a first lens set 11 with a positive focal power, a second lens set 12 with a positive focal power, a third lens set 13 with a positive focal power, and a fourth lens set 14 with a positive focal power from the object side along the same optical axis (that is, the optical axis A). The first lens set 11 is sequentially formed from the object side by a second lens 112 with a plane facing the object side and the third lens 113 with a convex surface facing the image side without the first lens 111, and immersed in normal saline before specific imaging to form a layer of normal saline on the surface of the second lens 112 facing the object side. The second lens set 12 is sequentially formed along the object side through fitting between a fourth lens 121 with a convex surface facing the object side and a fifth lens 122 with a convex surface facing the image side. The third lens set 13 is formed by a sixth lens 131 with a convex surface facing the object side. The fourth lens set 14 is sequentially formed from the object side by a seventh lens 141 with a concave surface facing the object side and an eighth lens 142 with a convex surface facing the object side. The second lens 112 to the eighth lens 142 are all spherical lenses.

The basic parameter table of the optical elements included by the imaging mechanism 10 in Embodiment 1 shown in Table 1 includes serial number (i), curvature radius ($r_i$), central thickness ($D_i$), refractive index ($Nd_i$), and Abbe number ($vd_j$). The optical elements refer to the normal saline and the second lens 112 to the eighth lens 142. In the basic parameter table, the column labeled serial number (i) indicates numbering the surfaces of optical elements starting from a surface of an optical element closest to the object side as the first surface to the surface, which is incremented sequentially towards the image side, as the i-th surface (i=1, 2, 3, . . . ). The fitting surfaces of two optical elements are defined as one surface (for example, the fourth lens 121 fits with the fifth lens 122, and the surface of the fourth lens 121 facing the image side and the surface of the fifth lens 122 facing the object side are defined as one surface). Moreover, the surface of the normal saline facing the image side and the surface of the second lens 112 facing the object side are defined as one surface. The column labeled curvature radius ($r_i$) represents a curvature radius of an i-th surface, and the symbol of the curvature radius ($r_i$) is positive when the surface facing the object side protrudes and is negative when the surface facing the image side protrudes. In the column labeled central thickness ($D_i$), $D_1$ represents a distance (that is, a central thickness of the normal saline) corresponding to a gap between the first surface center position and the second surface center position, $D_2$ represents a distance (that is, a central thickness of the second lens 112) corresponding to a gap between the second surface center position and the third surface center position, and $D_3$ represents a distance (that is, an air gap between the second lens 112 and the third lens 113) corresponding to a gap between the third surface center position and the fourth surface center position. By analog, $D_{13}$ represents a distance corresponding to a gap between the 13th surface center position and the 14th surface center position, and $D_{14}$ represents a distance corresponding to a gap between the 14th surface center position and an image surface formed by the biological body. The column labeled refractive index ($Nd_i$) represents a refractive index between the i-th surface and the i+1-th surface. $Nd_1$ represents a refractive index (that is, the refractive index of the normal saline) between the first surface and the second surface. $Nd_2$ represents a refractive index (that is, the refractive index of the second lens 112) between the second surface and the third surface. $Nd_3$ represents a refractive index (that is, the refractive index of air between the second lens 112 and the third lens 113) between the third refractive index and the fourth refractive index, . . . , by analog. Abbe number ($vd_j$) represents the Abbe number of the j-th (j=1, 2, 3, . . . ) optical element, and the Abbe number is recorded at the serial number corresponding to the surface of the optical element facing the object side.

It should be noted that i is specifically defined sequentially from the object side to the image side in the foregoing description. The surface of the normal saline facing the object side is defined as the first surface (that is, i=1). Because the normal saline fits with the second lens 112, the surface of the normal saline facing the image side fits with the surface of the second lens 112 facing the object side, and the two surfaces (that is, the surface of the normal saline facing the image side and the surface of the second lens 112 facing the object side) are defined as one surface, that is, the second surface (that is, i=2). The surface of the second lens 112 facing the image side is defined as the third surface (that is, i=3). The surface of the third lens 113 facing the object side is defined as the fourth surface (that is, i=4), . . . , by analog. j is specifically defined sequentially from the object side to the image side. The normal saline is defined as the first optical element (that is, j=1), and the Abbe number corresponding to the first optical element is filled in the column corresponding to the surface (that is, i=1) of the normal saline facing the object side. The second lens 112 is defined as the second optical element (that is, j=2), and the Abbe number corresponding to the second optical element is filled in the column corresponding to the surface (that is, i=2) of the second lens 112 facing the object side. The third lens 113 is defined as the third optical element (that is, j=3), and the Abbe number corresponding to the third optical element is filled in the column corresponding to the surface (that is, i=4) of the third lens 113 facing the object side, . . . , by analog.

The imaging mechanism 10 in Embodiment 1 has a numerical aperture (NA) of 0.5, a field of view of 0.5 (in the unit of, millimeter, mm) in the object space, telecentricity smaller than 0.2 (in the unit of, degree, °) in the image space, and an operating distance of 0.5 (in the unit of, millimeter, mm). "Millimeter" (abbreviated as "mm") is used as the length unit for the numerical values in Table 1, but used once as an example. The unit may be proportionally enlarged or reduced, allowing for the use of other appropriate units as well. Meanwhile, Table 1 shows the values rounded to numbers with specified decimal places.

TABLE 1

| Serial number (i) | Curvature radius ($r_i$) | Central thickness ($D_i$) | Refractive index ($Nd_i$) | Abbe number ($vd_j$) |
|---|---|---|---|---|
| 1 | ∞ | 0.5 | 1.333044 | 55.794 |
| 2 | ∞ | 2.503 | 1.891899 | 37.134 |
| 3 | −2.562 | 1.624 | 1.0 | |
| 4 | 10.108 | 2.432 | 1.528410 | 76.453 |
| 5 | −5.901 | 0.12 | 1.0 | |
| 6 | 6.446 | 0.949 | 1.854779 | 24.799 |
| 7 | 2.303 | 1.525 | 1.528410 | 76.453 |
| 8 | −11.7 | 0.119 | 1.0 | |
| 9 | 2.704 | 2.5 | 1.755000 | 52.319 |
| 10 | 1.712 | 1.025 | 1.0 | |
| 11 | −0.842 | 1.911 | 1.854779 | 24.799 |
| 12 | −2.331 | 0.12 | 1.0 | |
| 13 | 3.449 | 1.663 | 1.963000 | 24.114 |
| 14 | 12.021 | 1.012 | | |

Table 2 shows calculated values of each optical element in Embodiment 1.

TABLE 2

| $f_1/T$ | $f_2/f_1$ | $f_2/f_3$ | $f_4/f_1$ | $f_{42}/f_{41}$ | $r_3/f_{12}$ | $r_9/f_3$ | $r_{12}/r_{13}$ | $D_9/T$ | $\frac{r_4}{(H+H_1)}$ |
|---|---|---|---|---|---|---|---|---|---|
| 0.155 | 8.63 | 3.69 | 2.04 | −0.83 | −0.9 | 0.32 | −0.68 | 0.14 | 4.76 |

Figure 10:
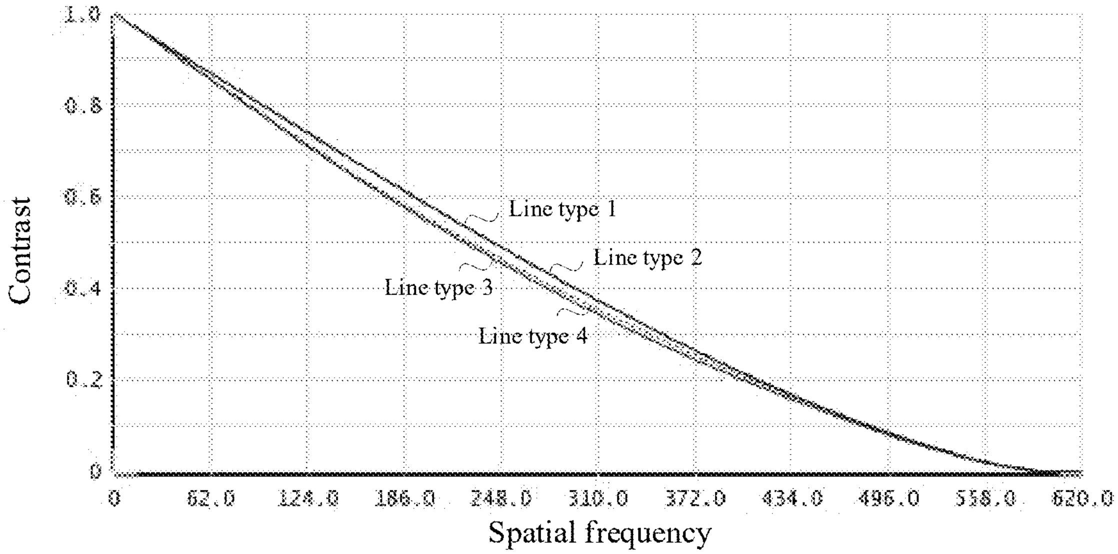
FIG. 10 is an MTF graph of an imaging mechanism at a field of view of 1.0 according to Embodiment 1.

Referring to FIG. 10, FIG. 10 is an MTF graph of an imaging mechanism 10 at a field of view of 1.0 according to Embodiment 1.

The abscissa in FIG. 10 represents spatial frequency in the unit of cycles per millimeter (cycles/mm). In FIG. 10, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.988823, 0.977607, 0.966306, 0.954857, 0.943218, 0.931446, 0.919606, 0.907723, 0.895815, 0.883894, 0.871974, 0.860067, 0.848184, 0.836321, 0.824479, 0.812669, 0.800896, 0.789156, 0.77745, 0.765788, 0.754175, 0.742606, 0.731084, 0.719625, 0.708231, 0.696881, 0.685578, 0.674352, 0.66327, 0.652425, 0.641792, 0.631215, 0.620642, 0.610128, 0.599697, 0.589337, 0.579027, 0.568738, 0.558492, 0.54835, 0.538362, 0.528566, 0.518897, 0.509231, 0.499553, 0.489911, 0.480318, 0.470768, 0.461231, 0.451676, 0.442163, 0.43278, 0.423547, 0.414444, 0.405416, 0.3964, 0.38737, 0.378332, 0.369378, 0.360603, 0.351959, 0.34338, 0.334903, 0.326574, 0.318381, 0.310292, 0.302268, 0.294265, 0.286253, 0.278243, 0.270358, 0.262673, 0.255074, 0.247489, 0.240026, 0.232737, 0.225502, 0.218265, 0.211146, 0.204185, 0.197247, 0.190284, 0.183432, 0.176724, 0.170008, 0.16325, 0.156603, 0.15009, 0.143546, 0.136956, 0.130489, 0.124154, 0.117776, 0.111362, 0.10511, 0.098996, 0.092797, 0.086605, 0.080767, 0.075238, 0.069677, 0.064096, 0.058738, 0.053541, 0.048263, 0.043071, 0.038322, 0.033842, 0.029222, 0.024744, 0.020941, 0.017522, 0.013924, 0.010467, 0.007711, 0.005253, 0.002545, 0.000453, 0.000004, 0.000351, 0.000301, 0.000007, 0, 0. Actual values (that is, ordinate values) on the Y-axis corresponding to line type 4 (actual transfer function in the sagittal direction) are respectively as follows: 1, 0.988892, 0.977776, 0.966632, 0.955391, 0.943999, 0.932501, 0.920949, 0.909359, 0.89774, 0.886098, 0.874441, 0.862781, 0.851126, 0.839473, 0.827823, 0.816189, 0.804579, 0.792988, 0.781421, 0.769889, 0.7584, 0.74695, 0.735542, 0.724192, 0.712904, 0.701665, 0.69047, 0.679338, 0.668337, 0.657586, 0.647066, 0.636607, 0.626152, 0.615757, 0.605446, 0.595206, 0.585021, 0.574866, 0.564755, 0.554727, 0.544852, 0.535206, 0.525717, 0.516236, 0.506742, 0.497288, 0.487889, 0.478535, 0.469196, 0.459846, 0.450529, 0.441313, 0.432249, 0.423361, 0.414568, 0.405764, 0.396927, 0.388072, 0.379277, 0.370615, 0.362081, 0.35365, 0.345304, 0.33704, 0.328896, 0.320893, 0.312944, 0.304961, 0.29692, 0.288844, 0.280846, 0.272999, 0.265232, 0.257493, 0.249839, 0.242297, 0.234805, 0.227333, 0.219948, 0.212671, 0.20542, 0.198171, 0.191011, 0.183959, 0.176913, 0.169856, 0.162897, 0.156051, 0.149196, 0.142326, 0.135575, 0.128947, 0.122296, 0.115638, 0.109149, 0.102796, 0.096362, 0.089939, 0.08387, 0.078134, 0.072435, 0.066767, 0.06132, 0.056009, 0.050597, 0.045268, 0.040416, 0.035845, 0.031107, 0.026501, 0.022598, 0.019086, 0.015367, 0.011811, 0.009039, 0.00653, 0.003578, 0.001092, 0.000225, 0.000296, 0.000237, 0.000044, 0, 0.

Figure 11:
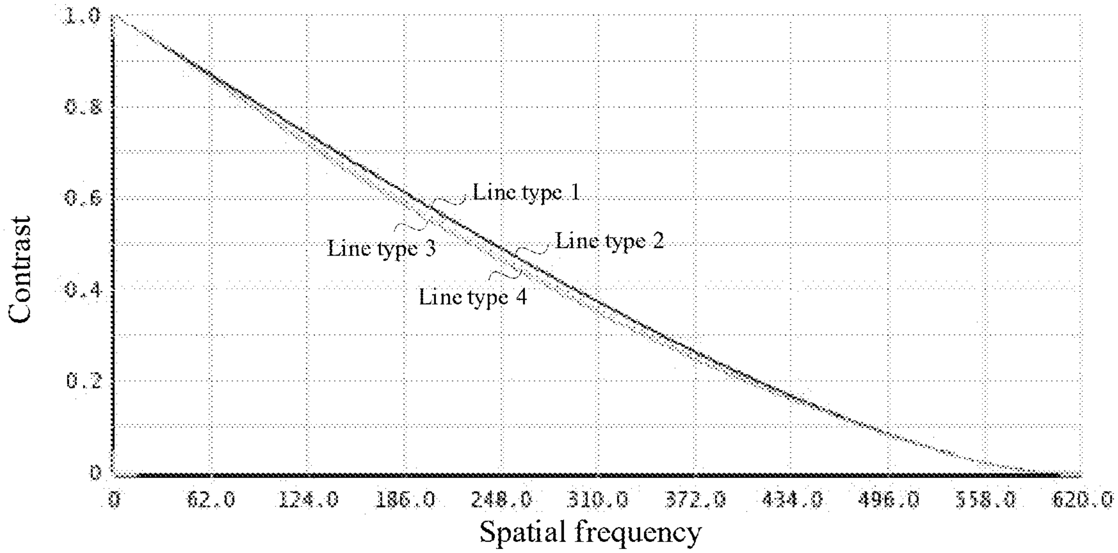
FIG. 11 is an MTF graph of an imaging mechanism at a field of view of 0.707 according to Embodiment 1.

Referring to FIG. 11, FIG. 11 is an MTF graph of an imaging mechanism 10 at a field of view of 0.707 according to Embodiment 1.

The abscissa in FIG. 11 represents spatial frequency in the unit of cycles per millimeter (cycles/mm). In FIG. 11, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.989015, 0.978098, 0.967277, 0.956424, 0.945424, 0.934297, 0.923081, 0.911776, 0.900377, 0.888896, 0.877344, 0.865731, 0.854066, 0.842361, 0.830629, 0.818881, 0.80713, 0.795387, 0.783664, 0.771972, 0.760321, 0.748716, 0.737167, 0.725687, 0.714278, 0.702931, 0.691646, 0.680437, 0.669372, 0.658568, 0.648003, 0.637504, 0.627013, 0.616586, 0.606244, 0.595972, 0.585747, 0.575546, 0.565382, 0.555294, 0.545349, 0.535616, 0.526023, 0.51642, 0.506787, 0.497179, 0.487608, 0.478064, 0.468516, 0.45894, 0.449381, 0.439914, 0.430587, 0.421417, 0.412327, 0.403218, 0.394067, 0.384893, 0.375777, 0.366803, 0.35796, 0.349213, 0.340559, 0.332008, 0.323591, 0.315322, 0.307123, 0.298915, 0.290673, 0.282421, 0.27428, 0.266331, 0.258489, 0.250699, 0.243031, 0.235523, 0.228095, 0.220712, 0.213455, 0.206351, 0.199302, 0.192273, 0.185369, 0.178609, 0.171874, 0.165136, 0.15852, 0.152038, 0.14555, 0.13904, 0.132657, 0.126401, 0.120105, 0.113779, 0.107612, 0.101567, 0.095406, 0.089223, 0.08338, 0.077847, 0.072297, 0.066729, 0.061362, 0.056111, 0.050721, 0.045387, 0.040522, 0.035928, 0.031142, 0.026477, 0.022532, 0.018989, 0.015224, 0.011625, 0.008835, 0.006328, 0.003389, 0.000947, 0.00017, 0.000314, 0.000246, 0.000014, 0, 0. Actual values (that is, ordinate values) on the Y-axis corresponding to line type 4 (actual transfer function in the sagittal direction) are respectively as follows: 1, 0.989055, 0.978203, 0.967487, 0.956783, 0.94597, 0.935068, 0.924118, 0.913114, 0.90205, 0.890932, 0.879768, 0.868562, 0.857319, 0.846047, 0.834752, 0.823443, 0.812128, 0.800814, 0.789508, 0.778221, 0.766957, 0.755722, 0.744522, 0.733366, 0.722259, 0.711192, 0.700164, 0.68918, 0.678309, 0.667677, 0.657267, 0.646901, 0.636521, 0.626185, 0.615915, 0.605695, 0.595507, 0.585333, 0.575183, 0.565086, 0.555115, 0.545355, 0.535737, 0.526103, 0.516434, 0.506785, 0.497172, 0.487581, 0.477989, 0.468372, 0.458768, 0.449241, 0.439848, 0.430628, 0.421495, 0.412337, 0.403138, 0.393921, 0.384752, 0.375702, 0.366779, 0.357972, 0.349252, 0.340603, 0.332081, 0.32372, 0.315428, 0.307109, 0.298748, 0.290373, 0.282086, 0.273958, 0.265936, 0.257981, 0.250127, 0.242395, 0.234743, 0.227156, 0.219673, 0.212307, 0.205003, 0.197743, 0.190586, 0.183545, 0.176543, 0.169565, 0.162692, 0.155932, 0.149188, 0.142453, 0.135832, 0.129324, 0.122807, 0.116293, 0.109928, 0.103678, 0.09735, 0.091027, 0.085015, 0.079301, 0.07363, 0.067992, 0.062542, 0.057196, 0.051746, 0.04637, 0.041437, 0.036768, 0.031952, 0.027269, 0.023257, 0.019631, 0.01584, 0.012236, 0.009398, 0.006825, 0.003843, 0.001308, 0.000313, 0.00027, 0.000219, 0.000081, 0.000012, 0.

Figure 12:
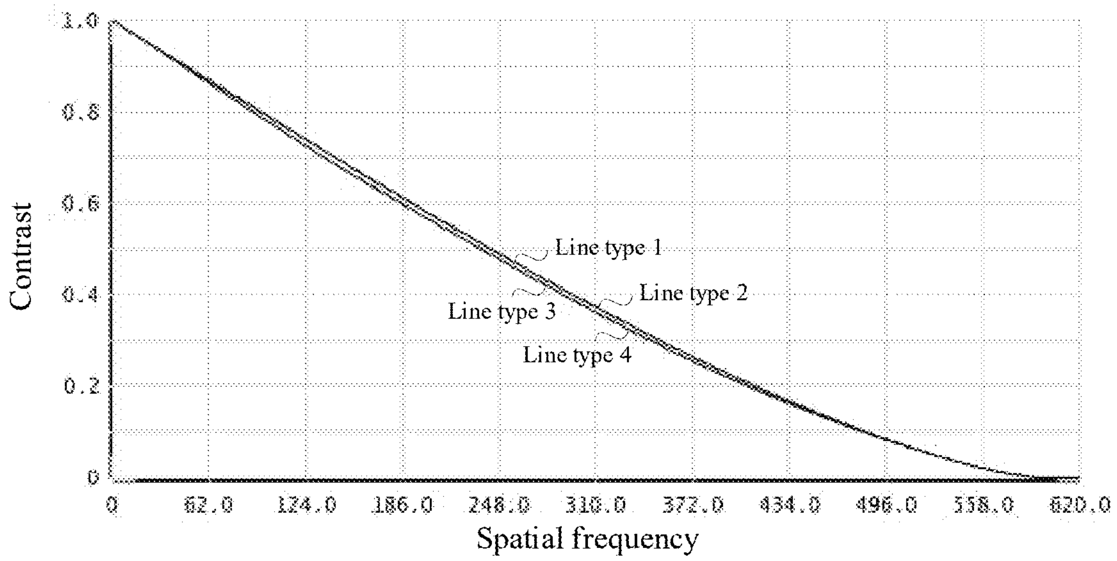
FIG. 12 is an MTF graph of an imaging mechanism at a central field of view according to Embodiment 1.

Referring to FIG. 12, FIG. 12 is an MTF graph of an imaging mechanism 10 at a central field of view according to Embodiment 1.

The abscissa in FIG. 12 represents spatial frequency in the unit of cycles per millimeter (cycles/mm). In FIG. 12, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.989061, 0.978207, 0.967478, 0.956748, 0.945899, 0.934956, 0.923957, 0.912905, 0.901796, 0.890642, 0.879456, 0.868245, 0.857018, 0.845786, 0.834559, 0.823345, 0.812153, 0.800991, 0.789866, 0.778784, 0.767751, 0.756767, 0.745838, 0.734969, 0.72416, 0.713403, 0.70269, 0.692023, 0.681463, 0.671142, 0.661037, 0.650971, 0.640879, 0.630819, 0.620809, 0.610832, 0.60087, 0.590906, 0.580945, 0.571011, 0.561178, 0.551539, 0.542024, 0.532471, 0.522859, 0.513247, 0.503648, 0.494048, 0.484425, 0.47476, 0.465085, 0.455456, 0.44594, 0.436582, 0.427297, 0.417967, 0.408576, 0.399155, 0.389762, 0.380459, 0.371271, 0.362198, 0.3532, 0.34425, 0.335415, 0.326747, 0.318146, 0.309511, 0.300834, 0.292147, 0.283545, 0.275093, 0.266761, 0.25852, 0.250387, 0.242373, 0.234463, 0.226652, 0.218957, 0.211385, 0.203905, 0.19651, 0.189235, 0.182083, 0.175007, 0.167997, 0.161106, 0.154336, 0.147619, 0.140948, 0.134397, 0.127963, 0.121549, 0.115167, 0.108928, 0.1028, 0.096616, 0.090448, 0.08456, 0.078949, 0.073404, 0.067907, 0.062568, 0.057307, 0.051946, 0.046654, 0.04176, 0.037108, 0.03233, 0.02768, 0.023647, 0.019979, 0.016188, 0.012594, 0.009717, 0.007094, 0.004106, 0.001539, 0.000411, 0.000243, 0.000196, 0.000118, 0.000052, 0. Actual values (that is, ordinate values) on the Y-axis corresponding to line type 4 (actual transfer function in the sagittal direction) are respectively as follows: 1, 0.989061, 0.978207, 0.967478, 0.956748, 0.945899, 0.934956, 0.923957, 0.912905, 0.901796, 0.890642, 0.879456, 0.868245, 0.857018, 0.845786, 0.834559, 0.823345, 0.812153, 0.800991, 0.789866, 0.778784, 0.767751, 0.756767, 0.745838, 0.734969, 0.72416, 0.713403, 0.70269, 0.692023, 0.681463, 0.671142, 0.661037, 0.650971, 0.640879, 0.630819, 0.620809, 0.610832, 0.60087, 0.590906, 0.580945, 0.571011, 0.561178, 0.551539, 0.542024, 0.532471, 0.522859, 0.513247, 0.503648, 0.494048, 0.484425, 0.47476, 0.465085, 0.455456, 0.44594, 0.436582, 0.427297, 0.417967, 0.408576, 0.399155, 0.389762, 0.380459, 0.371271, 0.362198, 0.3532, 0.34425, 0.335415, 0.326747, 0.318146, 0.309511, 0.300834, 0.292147, 0.283545, 0.275093, 0.266761, 0.25852, 0.250387, 0.242373, 0.234463, 0.226652, 0.218957, 0.211385, 0.203905, 0.19651, 0.189235, 0.182083, 0.175007, 0.167997, 0.161106, 0.154336, 0.147619, 0.140948, 0.134397, 0.127963, 0.121549, 0.115167, 0.108928, 0.1028, 0.096616, 0.090448, 0.08456, 0.078949, 0.073404, 0.067907, 0.062568, 0.057307, 0.051946, 0.046654, 0.04176, 0.037108, 0.03233, 0.02768, 0.023647, 0.019979, 0.016188, 0.012594, 0.009717, 0.007094, 0.004106, 0.001539, 0.000411, 0.000243, 0.000196, 0.000118, 0.000052, 0.

It should be noted that in FIGS. 10 to 12, line type 1 represents a diffraction-limited transfer function in the tangential direction, line type 2 represents the diffraction-limited transfer function in the sagittal direction, line type 3 represents the actual transfer function in the tangential direction, and line type 4 represents actual transfer function in the sagittal direction.

It can be known from FIGS. 10 to 12 that in the ideal state, optimal imaging effect with low distortion can be achieved when the transfer function in the tangential direction (that is, line type 1) coincides with the transfer function in the sagittal direction (that is, line type 2). In actual testing, when the ordinate values of line type 3 corresponding to the same abscissa value are closer to the ordinate values of line type 4, the actual transfer function in the tangential direction is more approximate to the actual transfer function in the sagittal direction. The MTF graph is typical at the central field of view in FIG. 12. In addition, considering the practical imaging, as ordinate values of line type 3 corresponding to the same abscissa value and the ordinate values of the line type 4 are respectively more approximate to the ordinate values of line type 1 and line type 2 at the same abscissa, the imaging effect is better, the image is more real, and the image has a lower distortion rate.

Figure 13:
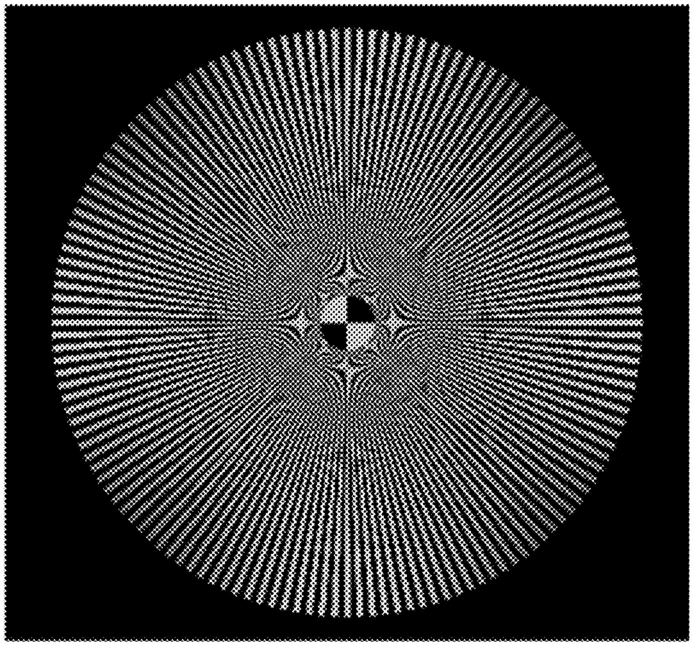
FIG. 13 is a Siemens star chart of an imaging mechanism according to Embodiment 1.

Referring to FIG. 13, FIG. 13 is a Siemens star chart of an imaging mechanism 10 according to Embodiment 1. It can be known from FIG. 13 that the Siemens star chart corresponding to the imaging mechanism 10 is clear. Better resolution and higher contrast indicate clearer imaging.

Unless specifically stated, the method, and symbols, meanings, and recording methods of various data of the imaging mechanism 10 in Embodiment 1 are equally applicable to the imaging system 10 in the following embodiments. Therefore, repetitive descriptions are omitted below.

Embodiment 2

The structure of the optical element of an imaging mechanism 10 in Embodiment 2 is shown in FIG. 9, and this structure is the same as that of the imaging mechanism 10 in Embodiment 1. For the method shown in the figure, reference is made to the foregoing description, and repeated description is omitted herein. The basic parameter table of the optical elements included by the imaging mechanism 10 in Embodiment 2 shown in Table 3 includes serial number (i), curvature radius ($r_i$), central thickness ($D_i$), refractive index ($Nd_i$), and Abbe number ($vd_j$).

The imaging mechanism 10 in Embodiment 2 has a numerical aperture (NA) of 0.5, a field of view of 0.5 mm in the object space, telecentricity smaller than 0.2° in the image space, and an operating distance of 1.989.

TABLE 3

| Serial number (i) | Curvature radius ($r_i$) | Central thickness ($D_i$) | Refractive index ($Nd_i$) | Abbe number ($vd_j$) |
|---|---|---|---|---|
| 1 | ∞ | 1.994 | 1.333044 | 55.794 |
| 2 | ∞ | 2.5 | 1.816000 | 46.621 |
| 3 | −3.774 | 0.12 | 1.0 | |
| 4 | 12.587 | 1.581 | 1.595220 | 67.736 |
| 5 | −7.354 | 0.118 | 1.0 | |
| 6 | 5.98 | 0.946 | 1.854779 | 24.799 |
| 7 | 2.31 | 1.619 | 1.497003 | 81.138 |
| 8 | −14.931 | 0.139 | 1.0 | |
| 9 | 2.042 | 2.509 | 1.618000 | 63.334 |
| 10 | 1.796 | 1.111 | 1.0 | |
| 11 | −0.919 | 1.161 | 1.89286 | 20.362 |
| 12 | −1.933 | 1.61 | 1.0 | |
| 13 | 3.397 | 1.598 | 2.003300 | 28.273 |
| 14 | 8.436 | 1 | | |

Table 4 shows calculated values of each optical element in Embodiment 2.

TABLE 4

| $f_1/T$ | $f_2/f_1$ | $f_2/f_3$ | $f_4/f_1$ | $f_{42}/f_{41}$ | $r_3/f_{12}$ | $r_9/f_3$ | $r_{12}/r_{13}$ | $D_9/T$ | $\frac{r_4}{(H+H_1)}$ |
|---|---|---|---|---|---|---|---|---|---|
| 0.173 | 11.03 | 4.15 | 2.14 | −0.88 | −0.82 | 0.25 | −0.57 | 0.14 | 5.95 |

Figure 14:
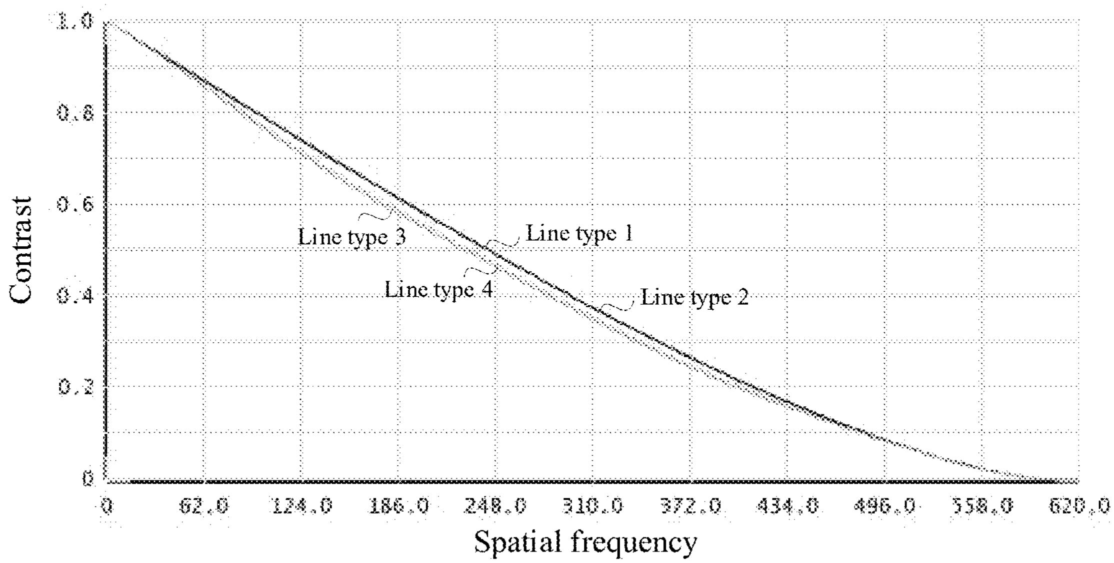
FIG. 14 is an MTF graph of an imaging mechanism at a field of view of 0.707 according to Embodiment 2.
Figure 15:
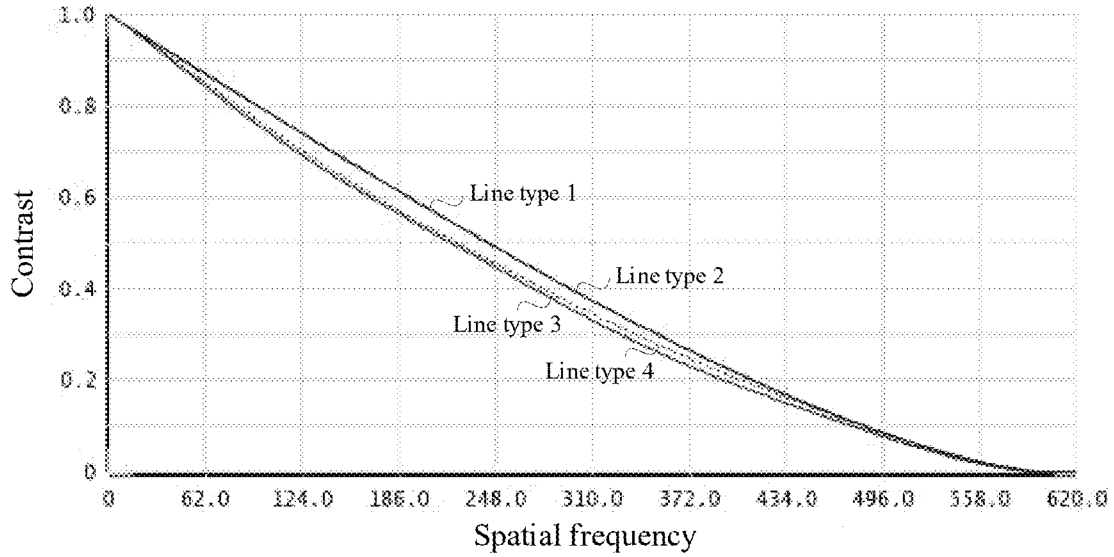
FIG. 15 is an MTF graph of an imaging mechanism at a field of view of 1.0 according to Embodiment 2.
Figure 16:
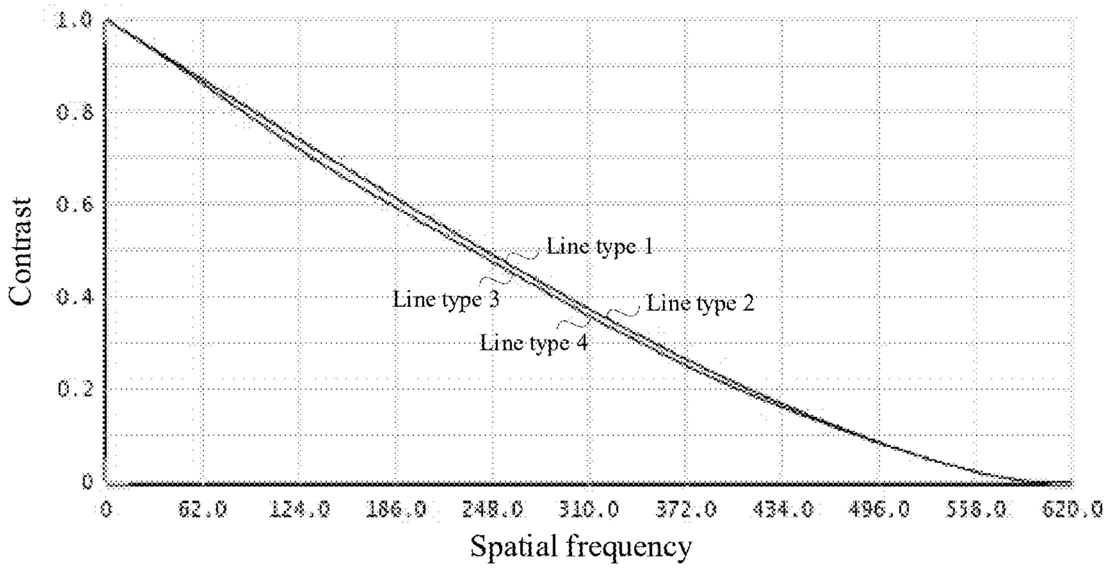
FIG. 16 is an MTF graph of an imaging mechanism at a central field of view according to Embodiment 2.

Referring to FIGS. 14 to 16, FIGS. 14 to 16 are respective MTF graphs of an imaging mechanism 10 at a field of view of 0.707, a field of view of 1.0, and a central field of view.

Figure 17:
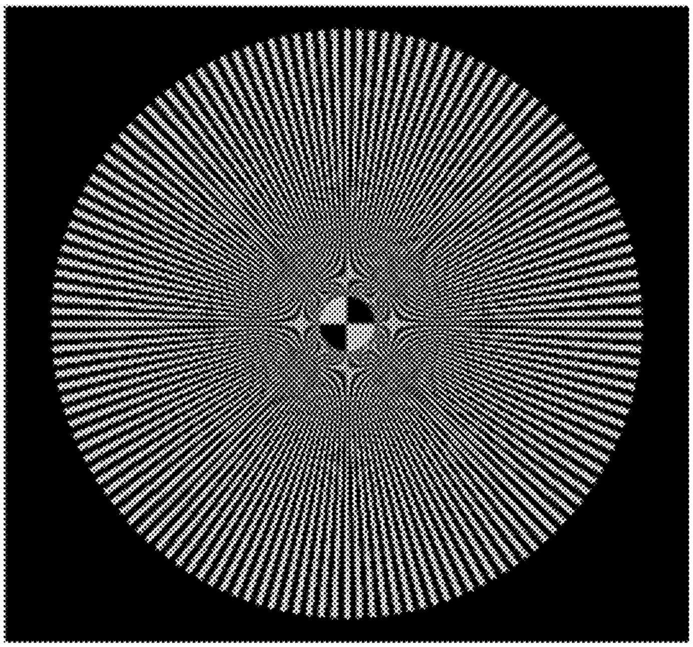
FIG. 17 is a Siemens star chart of an imaging mechanism according to Embodiment 2.

Referring to FIG. 17, FIG. 17 is a Siemens star chart of an imaging mechanism 10 according to Embodiment 2.

The abscissa in FIG. 14 represents spatial frequency in the unit of cycles per millimeter (cycles/mm). In FIG. 14, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.988939, 0.977875, 0.966782, 0.955542, 0.944059, 0.932363, 0.920499, 0.908478, 0.896309, 0.884016, 0.871623, 0.859148, 0.846613, 0.834041, 0.821455, 0.808877, 0.796328, 0.78383, 0.771402, 0.759065, 0.746835, 0.734722, 0.722741, 0.710908, 0.699228, 0.687692, 0.676296, 0.665056, 0.654033, 0.643341, 0.632952, 0.622689, 0.612485, 0.602388, 0.592413, 0.582536, 0.572729, 0.562959, 0.55323, 0.543577, 0.534058, 0.524736, 0.515537, 0.506303, 0.497011, 0.487711, 0.478415, 0.469107, 0.45976, 0.450345, 0.440908, 0.431524, 0.422243, 0.413085, 0.403976, 0.394819, 0.385596, 0.376328, 0.367101, 0.358001, 0.349023, 0.340142, 0.331355, 0.322675, 0.314142, 0.305774, 0.297498, 0.289237, 0.280972, 0.272728, 0.26463, 0.256758, 0.249032, 0.241399, 0.233928, 0.226652, 0.219496, 0.212423, 0.205509, 0.198775, 0.192125, 0.185522, 0.17906, 0.172753, 0.166481, 0.160213, 0.154062, 0.148036, 0.141993, 0.135916, 0.129941, 0.124066, 0.118124, 0.112126, 0.106253, 0.100467, 0.094534, 0.088547, 0.082865, 0.077462, 0.072019, 0.06654, 0.061241, 0.056041, 0.05069, 0.045386, 0.040541, 0.035959, 0.031183, 0.026525, 0.022582, 0.019036, 0.015272, 0.011673, 0.008881, 0.00637, 0.003427, 0.000975, 0.00018, 0.000311, 0.000245, 0.00002, 0, 0. Actual values (that is, ordinate values) on the Y-axis corresponding to line type 4 (actual transfer function in the sagittal direction) are respectively as follows: 1, 0.989007, 0.978053, 0.967146, 0.956168, 0.945015, 0.933717, 0.922315, 0.910813, 0.899211, 0.887519, 0.875753, 0.863924, 0.852043, 0.840126, 0.828188, 0.816245, 0.804313, 0.792409, 0.780547, 0.768743, 0.757012, 0.745361, 0.733801, 0.722346, 0.711, 0.699758, 0.688615, 0.677573, 0.666697, 0.656114, 0.645803, 0.635582, 0.625387, 0.615267, 0.605239, 0.595282, 0.585374, 0.575492, 0.565637, 0.55583, 0.54614, 0.536657, 0.527309, 0.517931, 0.5085, 0.499071, 0.489657, 0.480243, 0.470808, 0.46133, 0.451842, 0.4424, 0.433072, 0.423906, 0.414817, 0.405687, 0.396504, 0.387299, 0.378131, 0.369063, 0.360122, 0.351313, 0.342595, 0.333938, 0.325416, 0.31708, 0.308831, 0.300568, 0.292282, 0.284007, 0.275833, 0.267825, 0.259953, 0.252189, 0.244544, 0.237024, 0.229615, 0.222309, 0.21512, 0.208044, 0.201054, 0.194138, 0.187323, 0.180608, 0.173945, 0.16732, 0.160781, 0.154326, 0.147887, 0.141456, 0.135104, 0.128824, 0.122526, 0.116222, 0.110023, 0.103898, 0.097689, 0.091472, 0.08551, 0.079806, 0.074162, 0.068564, 0.063121, 0.057758, 0.052306, 0.046935, 0.041971, 0.03726, 0.032442, 0.027766, 0.02371, 0.020027, 0.016233, 0.012641, 0.009761, 0.007132, 0.004144, 0.001574, 0.000427, 0.000239, 0.000192, 0.000123, 0.000058, 0.

The abscissa in FIG. 15 represents spatial frequency in the unit of cycles per millimeter (cycles/mm). In FIG. 15, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.988603, 0.976989, 0.964987, 0.952579, 0.939807, 0.92678, 0.91361, 0.900372, 0.887122, 0.873901, 0.860743, 0.847683, 0.834742, 0.821919, 0.809214, 0.796645, 0.784221, 0.77193, 0.759768, 0.747748, 0.735874, 0.724134, 0.712526, 0.701067, 0.689756, 0.678561, 0.667482, 0.656555, 0.645841, 0.635412, 0.62523, 0.615143, 0.605094, 0.595128, 0.585258, 0.575469, 0.565727, 0.555991, 0.546282, 0.536664, 0.527173, 0.517821, 0.508537, 0.499209, 0.48982, 0.480407, 0.470985, 0.461549, 0.452064, 0.442499, 0.432922, 0.423439, 0.414053, 0.404731, 0.395432, 0.386119, 0.376769, 0.367384, 0.358077, 0.348957, 0.339964, 0.331022, 0.322196, 0.313562, 0.30509, 0.296733, 0.288473, 0.280296, 0.27217, 0.264105, 0.25623, 0.248619, 0.241148, 0.233741, 0.226517, 0.219533, 0.212655, 0.205817, 0.199141, 0.19267, 0.186256, 0.179843, 0.17356, 0.167435, 0.161313, 0.155153, 0.149091, 0.143144, 0.137157, 0.131107, 0.125139, 0.119263, 0.113324, 0.107327, 0.101433, 0.095627, 0.089739, 0.083849, 0.078242, 0.072877, 0.067471, 0.062035, 0.056781, 0.051674, 0.046536, 0.041491, 0.03681, 0.032368, 0.027871, 0.023533, 0.019755, 0.016333, 0.012855, 0.009508, 0.006661, 0.004187, 0.001884, 0.000257, 0, 0.000079, 0.000118, 0.000003, 0, 0. Actual values (that is, ordinate values) on the Y-axis corresponding to line type 4 (actual transfer function in the sagittal direction) are respectively as follows: 1, 0.988998, 0.977829, 0.966366, 0.954627, 0.942664, 0.930531, 0.918278, 0.905941, 0.893547, 0.881114, 0.86866, 0.856206, 0.843771, 0.831356, 0.818969, 0.806632, 0.794361, 0.782155, 0.770018, 0.757976, 0.746041, 0.734206, 0.722474, 0.710869, 0.699397, 0.688036, 0.676781, 0.66565, 0.654706, 0.644064, 0.633697, 0.623437, 0.613218, 0.603087, 0.593059, 0.583122, 0.573252, 0.563417, 0.553624, 0.543908, 0.534335, 0.524978, 0.515764, 0.50654, 0.497283, 0.488043, 0.478834, 0.469646, 0.460452, 0.451226, 0.442008, 0.432868, 0.423862, 0.415018, 0.406259, 0.397478, 0.388657, 0.379815, 0.371026, 0.362368, 0.353843, 0.345435, 0.33712, 0.328893, 0.320801, 0.312875, 0.305024, 0.297159, 0.28926, 0.281353, 0.273544, 0.265906, 0.258376, 0.25091, 0.243548, 0.236312, 0.229149, 0.222036, 0.215021, 0.208115, 0.201249, 0.194399, 0.187633, 0.180962, 0.174296, 0.167614, 0.161008, 0.154485, 0.147938, 0.141355, 0.134857, 0.128443, 0.121983, 0.115492, 0.109131, 0.102871, 0.096514, 0.090149, 0.084102, 0.078362, 0.072662, 0.066999, 0.061543, 0.056212, 0.050789, 0.045458, 0.040594, 0.036011, 0.031281, 0.026689, 0.022782, 0.019261, 0.01555, 0.012006, 0.009227, 0.006699, 0.003735, 0.001219, 0.000276, 0.00028, 0.000227, 0.000067, 0, 0.

The abscissa in FIG. 16 represents spatial frequency in the unit of cycles per millimeter (cycles/mm). In FIG. 16, the spatial frequency ranges from 0 to 620, with intervals of 5 cycles per millimeter. Actual values (that is, ordinate values) on the Y-axis corresponding to line type 3 (actual transfer function in the tangential direction) are respectively as follows: 1, 0.989048, 0.978154, 0.967336, 0.95647, 0.945441, 0.934274, 0.923009, 0.911646, 0.900187, 0.888646, 0.877041, 0.865384, 0.853691, 0.84198, 0.83027, 0.818577, 0.806917, 0.795307, 0.783762, 0.772296, 0.760919, 0.749638, 0.73846, 0.727395, 0.716444, 0.705601, 0.694856, 0.684203, 0.673702, 0.663485, 0.65353, 0.643652, 0.63378, 0.623966, 0.614222, 0.604527, 0.594858, 0.585196, 0.575537, 0.565895, 0.556341, 0.546975, 0.537727, 0.528426, 0.519049, 0.509652, 0.500247, 0.490817, 0.481345, 0.471813, 0.462246, 0.45269, 0.44322, 0.433901, 0.424643, 0.415317, 0.405916, 0.396477, 0.387048, 0.377679, 0.368416, 0.359283, 0.350221, 0.341184, 0.332262, 0.323527, 0.314872, 0.306183, 0.297467, 0.288761, 0.280143, 0.271671, 0.263346, 0.255156, 0.247087, 0.239132, 0.231312, 0.223639, 0.216093, 0.208663, 0.201356, 0.194178, 0.187118, 0.18017, 0.173321, 0.166569, 0.159922, 0.153371, 0.146887, 0.140466, 0.134135, 0.127882, 0.121658, 0.115469, 0.10938, 0.10336, 0.097293, 0.091239, 0.085397, 0.079783, 0.074266, 0.06882, 0.063486, 0.058196, 0.052834, 0.047545, 0.042597, 0.037871, 0.033081, 0.028434, 0.024319, 0.02055, 0.016749, 0.013169, 0.010216, 0.007502, 0.004522, 0.00193, 0.000589, 0.000201, 0.000154, 0.000171, 0.000115, 0. Actual values (that is, ordinate values) on the Y-axis corresponding to line type 4 (actual transfer function in the sagittal direction) are respectively as follows: 1, 0.989048, 0.978154, 0.967336, 0.95647, 0.945441, 0.934274, 0.923009, 0.911646, 0.900187, 0.888646, 0.877041, 0.865384, 0.853691, 0.84198, 0.83027, 0.818577, 0.806917, 0.795307, 0.783762, 0.772296, 0.760919, 0.749638, 0.73846, 0.727395, 0.716444, 0.705601, 0.694856, 0.684203, 0.673702, 0.663485, 0.65353, 0.643652, 0.63378, 0.623966, 0.614222, 0.604527, 0.594858, 0.585196, 0.575537, 0.565895, 0.556341, 0.546975, 0.537727, 0.528426, 0.519049, 0.509652, 0.500247, 0.490817, 0.481345, 0.471813, 0.462246, 0.45269, 0.44322, 0.433901, 0.424643, 0.415317, 0.405916, 0.396477, 0.387048, 0.377679, 0.368416, 0.359283, 0.350221, 0.341184, 0.332262, 0.323527, 0.314872, 0.306183, 0.297467, 0.288761, 0.280143, 0.271671, 0.263346, 0.255156, 0.247087, 0.239132, 0.231312, 0.223639, 0.216093, 0.208663, 0.201356, 0.194178, 0.187118, 0.18017, 0.173321, 0.166569, 0.159922, 0.153371, 0.146887, 0.140466, 0.134135, 0.127882, 0.121658, 0.115469, 0.10938, 0.10336, 0.097293, 0.091239, 0.085397, 0.079783, 0.074266, 0.06882, 0.063486, 0.058196, 0.052834, 0.047545, 0.042597, 0.037871, 0.033081, 0.028434, 0.024319, 0.02055, 0.016749, 0.013169, 0.010216, 0.007502, 0.004522, 0.00193, 0.000589, 0.000201, 0.000154, 0.000171, 0.000115, 0.

It should be noted that in FIGS. 14 to 16, line type 1 represents a diffraction-limited transfer function in the tangential direction, line type 2 represents the diffraction-limited transfer function in the sagittal direction, line type 3 represents the actual transfer function in the tangential direction, and line type 4 represents actual transfer function in the sagittal direction. It can be known from FIGS. 14 to 16 that in the ideal state, optimal imaging effect with low distortion can be achieved when the transfer function in the tangential direction (that is, line type 1) coincides with the transfer function in the sagittal direction (that is, line type 2). In actual testing, when the ordinate values of line type 3 corresponding to the same abscissa value are closer to the ordinate values of line type 4, the actual transfer function in the tangential direction is more approximate to the actual transfer function in the sagittal direction. In addition, considering the practical imaging, as ordinate values of line type 3 corresponding to the same abscissa value and the ordinate values of the line type 4 are respectively more approximate to the ordinate values of line type 1 and line type 2 at the same abscissa, the imaging effect is better, the image is more real, and the image has a lower distortion rate.

Embodiment 3

The structure of the optical element of an imaging mechanism 10 in Embodiment 2 is shown in FIG. 9, and this structure is the same as that of the imaging mechanism 10 in Embodiment 1. For the method shown in the figure, reference is made to the foregoing description, and repeated description is omitted herein. The basic parameter table of the optical elements included by the imaging mechanism 10 in Embodiment 3 shown in Table 5 includes serial number (i), curvature radius ($r_i$), central thickness ($D_i$), refractive index ($Nd_i$), and Abbe number ($vd_j$).

The imaging mechanism 10 in Embodiment 3 has a numerical aperture (NA) of 0.5, a field of view of 0.5 mm in the object space, telecentricity smaller than 0.2° in the image space, and an operating distance of 2.15 mm.

TABLE 5

| Serial number (i) | Curvature radius ($r_i$) | Central thickness ($D_i$) | Refractive index ($Nd_i$) | Abbe number ($vd_j$) |
|---|---|---|---|---|
| 1 | ∞ | 2.15 | 1.333044 | 55.794 |
| 2 | ∞ | 1.96 | 1.816000 | 46.621 |
| 3 | −3.546 | 0.141 | 1.0 | |
| 4 | 36.342 | 1.318 | 1.595220 | 67.736 |
| 5 | −5.794 | 0.115 | 1.0 | |
| 6 | 7.487 | 0.943 | 1.854779 | 24.799 |
| 7 | 2.26 | 2.308 | 1.595220 | 67.736 |
| 8 | −13.725 | 0.12 | 1.0 | |
| 9 | 2.013 | 2.494 | 1.622800 | 56.913 |
| 10 | 1.565 | 1.087 | 1.0 | |
| 11 | −0.855 | 1.031 | 1.854779 | 24.799 |
| 12 | −1.706 | 1.409 | 1.0 | |
| 13 | 3.163 | 1.711 | 1.816000 | 46.621 |
| 14 | 13.327 | 1.22 | | |

Table 6 shows calculated values of each optical element in Embodiment 3.

TABLE 6

| $f_1/T$ | $f_2/f_1$ | $f_2/f_3$ | $f_4/f_1$ | $f_{42}/f_{41}$ | $r_3/f_{12}$ | $r_9/f_3$ | $r_{12}/r_{13}$ | $D_9/T$ | $\frac{r_4}{(H+H_1)}$ |
|---|---|---|---|---|---|---|---|---|---|
| 0.170 | 7.2 | 2.24 | 1.99 | −0.96 | −0.82 | 0.20 | −0.54 | 0.14 | 15.86 |

Figure 18:
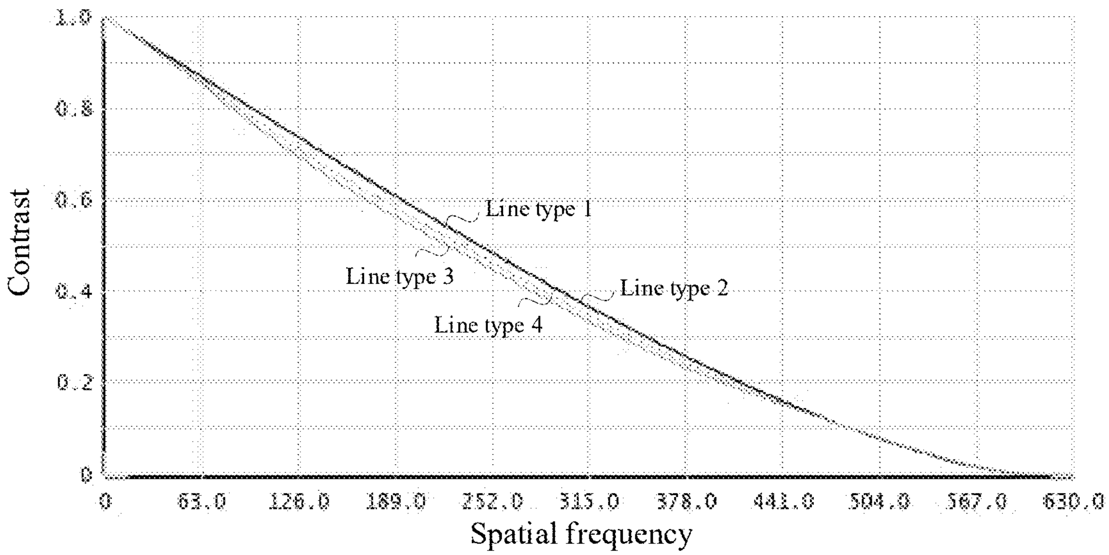
FIG. 18 is an MTF graph of an imaging mechanism at a field of view of 0.707 according to Embodiment 3.
Figure 19:
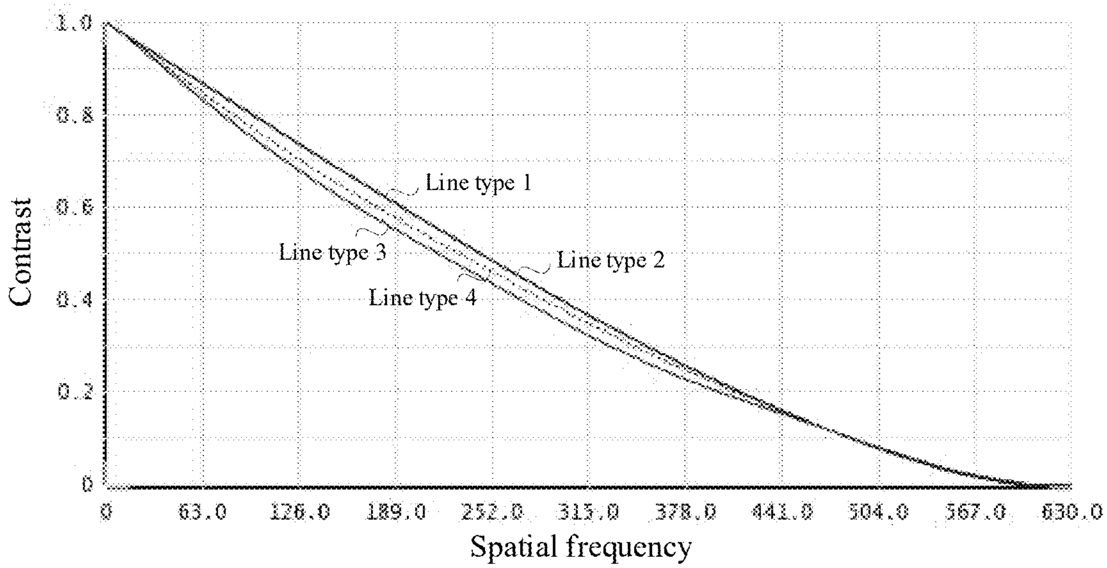
FIG. 19 is an MTF graph of an imaging mechanism at a field of view of 1.0 according to Embodiment 3.
Figure 20:
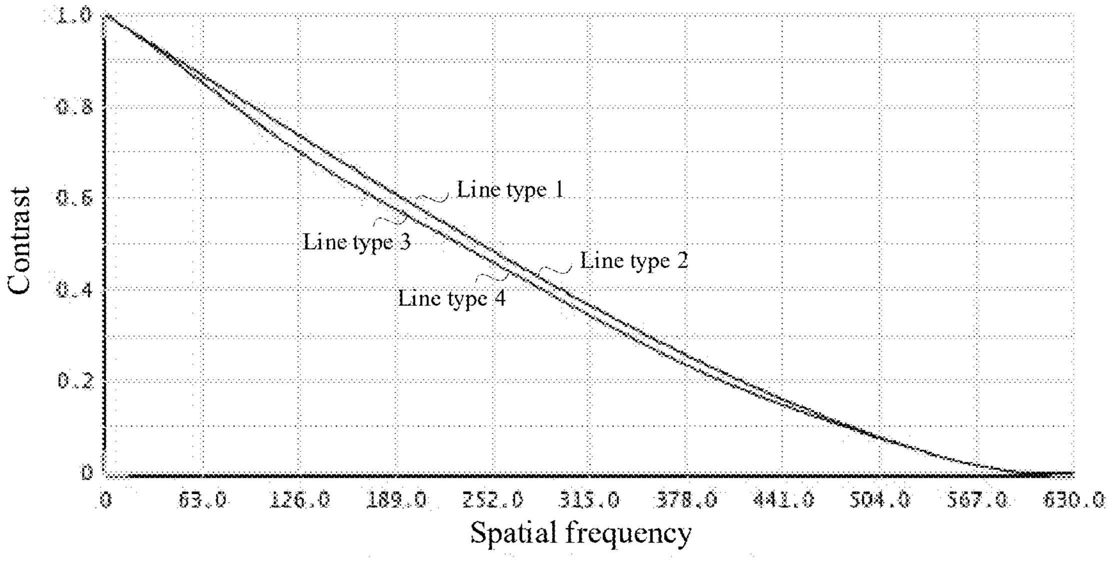
FIG. 20 is an MTF graph of an imaging mechanism at a central field of view according to Embodiment 3.
Figure 21:
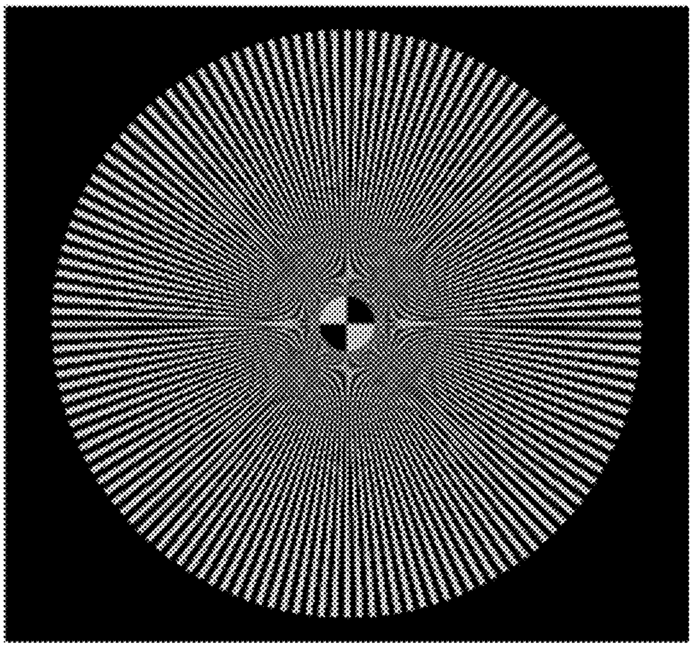
FIG. 21 is a Siemens star chart of an imaging mechanism according to Embodiment 3.

Referring to FIGS. 18 to 20, FIG. 18 is an MTF graph of an imaging mechanism 10 at a field of view of 0.707 according to Embodiment 3, FIG. 19 is an MTF graph of an imaging mechanism 10 at a field of view of 1.0 according to Embodiment 3, and FIG. 20 is an MTF graph of an imaging mechanism 10 at a central field of view according to Embodiment 3. Referring to FIG. 21, FIG. 21 is a Siemens star chart of an imaging mechanism 10 according to Embodiment 3.

The abscissa in FIG. 18 represents spatial frequency in the unit of cycles per millimeter (cycles/mm). In FIG. 18, the spatial frequency ranges from 0 to 630, with intervals of 5 cycles per millimeter. Actual values (that is, ordinate values) on the Y-axis corresponding to line type 3 (actual transfer function in the tangential direction) are respectively as follows: 1, 0.988963, 0.977883, 0.966706, 0.955349, 0.943742, 0.931908, 0.919885, 0.907686, 0.895322, 0.882814, 0.870187, 0.857467, 0.84468, 0.831857, 0.81903, 0.806228, 0.79348, 0.780815, 0.768257, 0.755832, 0.743558, 0.731448, 0.719512, 0.707768, 0.696227, 0.684867, 0.67367, 0.662667, 0.651902, 0.641439, 0.631304, 0.621373, 0.611517, 0.601746, 0.592091, 0.582544, 0.57308, 0.56365, 0.554225, 0.544861, 0.535626, 0.526532, 0.517561, 0.508615, 0.499606, 0.490544, 0.481463, 0.472368, 0.463248, 0.454058, 0.444777, 0.435507, 0.426349, 0.417277, 0.408235, 0.399186, 0.390098, 0.380939, 0.371711, 0.362552, 0.353578, 0.344694, 0.335798, 0.326987, 0.318367, 0.309883, 0.301457, 0.29308, 0.284754, 0.27644, 0.268129, 0.259978, 0.252115, 0.244399, 0.236695, 0.229145, 0.221891, 0.214786, 0.207682, 0.200725, 0.194057, 0.187521, 0.18096, 0.174518, 0.168339, 0.162261, 0.156118, 0.150056, 0.144217, 0.138439, 0.132559, 0.126717, 0.121058, 0.115426, 0.109668, 0.103922, 0.098328, 0.092733, 0.087008, 0.081407, 0.076157, 0.071015, 0.065714, 0.0604, 0.055249, 0.050164, 0.045054, 0.040099, 0.035468, 0.031004, 0.026564, 0.022389, 0.018708, 0.015309, 0.011967, 0.008822, 0.006049, 0.003586, 0.001439, 0.000128, 0.000016, 0.000327, 0.000253, 0, 0, 0. Actual values (that is, ordinate values) on the Y-axis corresponding to line type 4 (actual transfer function in the sagittal direction) are respectively as follows: 1, 0.989022, 0.978051, 0.967072, 0.95598, 0.944679, 0.933192, 0.921562, 0.909799, 0.897907, 0.885903, 0.873806, 0.861638, 0.849417, 0.837167, 0.824912, 0.812676, 0.800482, 0.788352, 0.776305, 0.764361, 0.752536, 0.740839, 0.729278, 0.717869, 0.706623, 0.695516, 0.684529, 0.673697, 0.663074, 0.652716, 0.642648, 0.632748, 0.622893, 0.613095, 0.603387, 0.593764, 0.584204, 0.574659, 0.565098, 0.55559, 0.546212, 0.53697, 0.527837, 0.518724, 0.509548, 0.50032, 0.491073, 0.481814, 0.472539, 0.463194, 0.453755, 0.444339, 0.435062, 0.425882, 0.416725, 0.407564, 0.398374, 0.389114, 0.379778, 0.37052, 0.361471, 0.352513, 0.343527, 0.334626, 0.325934, 0.317379, 0.30886, 0.300376, 0.291935, 0.283492, 0.275033, 0.266726, 0.258712, 0.250833, 0.242934, 0.235178, 0.227723, 0.220404, 0.213061, 0.205852, 0.198935, 0.192143, 0.185306, 0.178581, 0.172123, 0.165763, 0.159332, 0.152979, 0.146855, 0.140797, 0.134643, 0.128532, 0.122609, 0.116728, 0.110738, 0.104768, 0.098947, 0.093146, 0.087259, 0.081519, 0.076132, 0.070869, 0.065482, 0.060083, 0.054827, 0.049666, 0.044546, 0.039581, 0.034884, 0.03038, 0.025999, 0.021882, 0.018162, 0.014744, 0.011506, 0.008443, 0.005603, 0.003121, 0.001184, 0.000109, 0.000037, 0.000297, 0.000223, 0, 0, 0.

The abscissa in FIG. 19 represents spatial frequency in the unit of cycles per millimeter (cycles/mm). In FIG. 19, the spatial frequency ranges from 0 to 630, with intervals of 5 cycles per millimeter. Actual values (that is, ordinate values) on the Y-axis corresponding to line type 3 (actual transfer function in the tangential direction) are respectively as follows: 1, 0.988465, 0.976517, 0.963856, 0.950633, 0.937084, 0.923348, 0.909535, 0.895737, 0.882026, 0.868414, 0.854905, 0.841532, 0.828323, 0.81526, 0.802326, 0.789544, 0.776935, 0.764486, 0.752181, 0.740037, 0.728071, 0.716272, 0.704626, 0.693147, 0.681845, 0.670704, 0.659704, 0.648844, 0.638148, 0.627713, 0.617606, 0.607693, 0.597833, 0.588033, 0.578331, 0.568715, 0.55916, 0.549642, 0.54014, 0.530662, 0.521237, 0.511941, 0.502822, 0.493757, 0.484618, 0.475428, 0.466233, 0.457032, 0.447812, 0.438555, 0.429253, 0.419949, 0.410699, 0.401565, 0.392582, 0.383665, 0.374725, 0.365766, 0.356825, 0.347963, 0.339238, 0.330673, 0.322273, 0.31401, 0.305867, 0.297901, 0.290155, 0.282557, 0.275021, 0.267537, 0.260128, 0.252863, 0.245803, 0.238922, 0.232183, 0.225591, 0.219155, 0.212851, 0.206656, 0.200576, 0.194612, 0.188731, 0.1829, 0.177131, 0.171434, 0.165765, 0.160082, 0.154408, 0.148766, 0.143106, 0.137382, 0.131635, 0.125903, 0.120135, 0.114283, 0.10842, 0.102611, 0.096771, 0.090839, 0.084982, 0.079362, 0.073886, 0.068442, 0.0631, 0.057933, 0.05283, 0.047711, 0.042805, 0.038303, 0.033948, 0.029513, 0.025351, 0.02178, 0.018416, 0.014893, 0.011644, 0.009056, 0.006541, 0.003624, 0.001249, 0.000333, 0.000256, 0.000202, 0.000099, 0.000034, 0. Actual values (that is, ordinate values) on the Y-axis corresponding to line type 4 (actual transfer function in the sagittal direction) are respectively as follows: 1, 0.988684, 0.977182, 0.965353, 0.953247, 0.940955, 0.928565, 0.916153, 0.903772, 0.891459, 0.879214, 0.867038, 0.854949, 0.842964, 0.831066, 0.819236, 0.807491, 0.79585, 0.784299, 0.772822, 0.761436, 0.750161, 0.738983, 0.72789, 0.716902, 0.706037, 0.695264, 0.684559, 0.673956, 0.663508, 0.653283, 0.643316, 0.63349, 0.623681, 0.613903, 0.604194, 0.594553, 0.584964, 0.575387, 0.565795, 0.556248, 0.546817, 0.537531, 0.528384, 0.519278, 0.510119, 0.500925, 0.491735, 0.482556, 0.473379, 0.464161, 0.454883, 0.445644, 0.436543, 0.427568, 0.418677, 0.409817, 0.400937, 0.39201, 0.383044, 0.374166, 0.365483, 0.356914, 0.348367, 0.339913, 0.331632, 0.323487, 0.315416, 0.307383, 0.29936, 0.291306, 0.28322, 0.275248, 0.26751, 0.25987, 0.252195, 0.244616, 0.237258, 0.229982, 0.222647, 0.215391, 0.208349, 0.201368, 0.194297, 0.187284, 0.180476, 0.173709, 0.166824, 0.15998, 0.153335, 0.146721, 0.139975, 0.133264, 0.12676, 0.120294, 0.113703, 0.107166, 0.100859, 0.0946, 0.088231, 0.082061, 0.076374, 0.070891, 0.06531, 0.059799, 0.054557, 0.049437, 0.044302, 0.039385, 0.034897, 0.030593, 0.026251, 0.022187, 0.0187, 0.015471, 0.012174, 0.009059, 0.006402, 0.003981, 0.001662, 0.000148, 0, 0.00035, 0.000276, 0, 0, 0.

The abscissa in FIG. 20 represents spatial frequency in the unit of cycles per millimeter (cycles/mm). In FIG. 20, the spatial frequency ranges from 0 to 630, with intervals of 5 cycles per millimeter. Actual values (that is, ordinate values) on the Y-axis corresponding to line type 3 (actual transfer function in the tangential direction) are respectively as follows: 1, 0.989005, 0.977998, 0.966945, 0.95574, 0.944284, 0.932604, 0.920747, 0.908728, 0.896555, 0.884257, 0.871864, 0.859404, 0.846903, 0.834392, 0.821903, 0.809462, 0.797097, 0.78483, 0.772684, 0.760678, 0.748828, 0.73714, 0.72562, 0.714283, 0.703137, 0.692154, 0.68131, 0.670642, 0.6602, 0.650036, 0.640168, 0.630473, 0.620829, 0.611243, 0.601747, 0.592334, 0.582981, 0.573637, 0.564269, 0.554947, 0.545751, 0.536681, 0.527705, 0.518734, 0.509688, 0.500578, 0.491433, 0.482263, 0.47306, 0.463771, 0.454371, 0.44498, 0.435715, 0.426527, 0.417341, 0.40813, 0.398874, 0.389531, 0.380094, 0.37072, 0.361544, 0.352442, 0.343289, 0.334209, 0.325334, 0.316585, 0.307854, 0.299148, 0.290483, 0.281816, 0.273132, 0.264605, 0.256377, 0.24829, 0.240189, 0.232242, 0.224612, 0.217136, 0.20965, 0.202316, 0.195298, 0.188427, 0.181535, 0.174777, 0.168309, 0.161965, 0.155578, 0.149291, 0.143252, 0.137301, 0.131281, 0.125321, 0.119557, 0.11385, 0.108056, 0.102286, 0.096656, 0.091054, 0.085385, 0.079857, 0.074655, 0.069565, 0.064351, 0.059108, 0.053974, 0.048926, 0.043929, 0.039067, 0.034423, 0.029964, 0.025662, 0.021608, 0.017894, 0.01448, 0.011296, 0.008276, 0.005411, 0.002924, 0.001084, 0.000112, 0.000051, 0.000281, 0.000207, 0, 0, 0. Actual values (that is, ordinate values) on the Y-axis corresponding to line type 4 (actual transfer function in the sagittal direction) are respectively as follows: 1, 0.989005, 0.977998, 0.966945, 0.95574, 0.944284, 0.932604, 0.920747, 0.908728, 0.896555, 0.884257, 0.871864, 0.859404, 0.846903, 0.834392, 0.821903, 0.809462, 0.797097, 0.78483, 0.772684, 0.760678, 0.748828, 0.73714, 0.72562, 0.714283, 0.703137, 0.692154, 0.68131, 0.670642, 0.6602, 0.650036, 0.640168, 0.630473, 0.620829, 0.611243, 0.601747, 0.592334, 0.582981, 0.573637, 0.564269, 0.554947, 0.545751, 0.536681, 0.527705, 0.518734, 0.509688, 0.500578, 0.491433, 0.482263, 0.47306, 0.463771, 0.454371, 0.44498, 0.435715, 0.426527, 0.417341, 0.40813, 0.398874, 0.389531, 0.380094, 0.37072, 0.361544, 0.352442, 0.343289, 0.334209, 0.325334, 0.316585, 0.307854, 0.299148, 0.290483, 0.281816, 0.273132, 0.264605, 0.256377, 0.24829, 0.240189, 0.232242, 0.224612, 0.217136, 0.20965, 0.202316, 0.195298, 0.188427, 0.181535, 0.174777, 0.168309, 0.161965, 0.155578, 0.149291, 0.143252, 0.137301, 0.131281, 0.125321, 0.119557, 0.11385, 0.108056, 0.102286, 0.096656, 0.091054, 0.085385, 0.079857, 0.074655, 0.069565, 0.064351, 0.059108, 0.053974, 0.048926, 0.043929, 0.039067, 0.034423, 0.029964, 0.025662, 0.021608, 0.017894, 0.01448, 0.011296, 0.008276, 0.005411, 0.002924, 0.001084, 0.000112, 0.000051, 0.000281, 0.000207, 0, 0, 0.

It should be noted that in FIGS. 18 to 20, line type 1 represents a diffraction-limited transfer function in the tangential direction, line type 2 represents the diffraction-limited transfer function in the sagittal direction, line type 3 represents the actual transfer function in the tangential direction, and line type 4 represents actual transfer function in the sagittal direction. It can be known from FIGS. 18 to 20 that in the ideal state, optimal imaging effect with low distortion can be achieved when the transfer function in the tangential direction (that is, line type 1) coincides with the transfer function in the sagittal direction (that is, line type 2). In actual testing, when the ordinate values of line type 3 corresponding to the same abscissa value are closer to the ordinate values of line type 4, the actual transfer function in the tangential direction is more approximate to the actual transfer function in the sagittal direction. In addition, considering the practical imaging, as ordinate values of line type 3 corresponding to the same abscissa value and the ordinate values of the line type 4 are respectively more approximate to the ordinate values of line type 1 and line type 2 at the same abscissa, the imaging effect is better, the image is more real, and the image has a lower distortion rate.

As shown in FIGS. 2 and 6, the coaxial optical system 100 further includes a lens base 50 configured at an outer lens sheath image-side end 423 and an adapter base 43 detachably connected to the lens base 50. The outer lens sheath 42 is mounted at and detachably connected to the lens base 50 using the adapter base 43. Detachable connection between the adapter base 43 and the lens base 50 may be but is not limited to snap-fitting, threading, or bolting.

As shown in FIG. 6, the lens base 50 is constructed with an accommodating channel 51 accommodating at least part of the transfer lens sheath 301, and the accommodating channel 51 forms radially inwards a step recess 52 for a transfer lens sheath image-side end 3013 to axially abut against. The inner lens sheath 41 axially penetrates through the adapter base 43 and extends into the lens base 50, so as to abut against the step recess 52 formed by the lens base 50, and the inner lens sheath 41 is axially abutted between the lens base 50 and the outer abutting portion 21. As the accommodating channel 51 accommodates at least the part of the transfer lens sheath 301 and the inner lens sheath 41, the accommodating channel 51 can collimate the rod-shaped lens set 311 in the transfer lens sheath 301, improving the coaxial length between rod-shaped lens sets 311. A larger axial length of the accommodating channel 51 indicates higher coaxiality between the rod-shaped lens sets 311. The inner lens sheath 41 is axially abutted between the lens base 50 and the outer abutting portion 21, so as to improve the stability of mounting the inner lens sheath 41.

Based on the technical solution of any one of the coaxial optical systems 100 disclosed in the foregoing embodiments and the reasonable combination thereof, this embodiment further discloses an endoscopic imaging system 200.

The endoscopic imaging system 200 includes a lens base 50 with a dichroscope 70, a light source 60, and the coaxial optical system 100 as disclosed in the foregoing embodiment. The lens base 50 included by the coaxial optical system 100 receives light incident from the light source 60 onto the dichroscope 70, and after reflection by the dichroscope 70, the coaxial optical system 100 captures the light reflected again by an object W under test (which includes a living creature or a detached biological tissue). The reflected light penetrates through the dichroscope 70 to be captured by the endoscopic imaging system 200.

The lens base 50 is arranged to receive light rays incident onto the dichroscope 70 from the light source 60 along the direction indicated by arrow R1 in FIG. 3. Then, the light rays are reflected by the dichroscope 70 along the direction indicated by arrow R2 in FIG. 3, sequentially enter into the transfer mechanism 30 and the imaging mechanism 10 included by the coaxial optical system 100, and are gathered by the imaging mechanism 10 on the object W under test. Next, the light rays are reflected by the tissue surface of the object W under test, and the imaging mechanism 10 gathers the light rays reflected by the object W under test for imaging. The transfer mechanism 30 transmits the image generated by the imaging mechanism 10 in proportion. The reflected light rays penetrate through the dichroscope 70 along the direction indicated by the arrow R3 in FIG. 3 to be captured by the endoscopic imaging system 200, thus allowing the operator (for example, medical personnel or scientific researcher) to observe the image of the biological body.

Based on the endoscopic imaging system 200 disclosed in the foregoing embodiment, this embodiment further discloses application of the endoscopic imaging system. The endoscopic imaging system 200 disclosed in the foregoing embodiments is used to optically image tissue of the biological body (which includes a living creature or a detached biological tissue), thus allowing the operator (for example, medical personnel or scientific researcher) to observe the image of the biological body. For details, references may be made to the foregoing description, and details are not repeated.

The series of detailed descriptions listed in the preceding text are only specific explanations for the feasible implementations of the present invention. They are not intended to limit the protection scope of the present invention. Equivalent implementations or modifications made within the spirit of the technical concept of the present invention should be included in the protection scope of the present invention.

For those skilled in the art, it is apparent that the present invention is not limited to the details of the exemplary embodiments mentioned above. Moreover, the present invention can be implemented in other specific forms without departing from the spirit or basic feature of the present invention. Therefore, from any perspective, the embodiments should be regarded as exemplary and non-limiting. The scope of the present invention is defined by the appended claims rather than the above description. Therefore, it is intended to encompass all changes in the meaning and scope of the equivalent elements of the claims within the present invention. Any reference signs in the claims should not be construed as limitation on the related claims. Additionally, it should be understood that though this specification is described according to the implementations, not every implementation merely includes a single independent technical solution. This manner of description in the specification is solely for clarity. Those skilled in the art should consider the specification as a whole, and the technical solutions in various embodiments can also be appropriately combined to form other implementations understandable by those skilled in the art.

What claimed is:

1. A coaxial endoscopic optical system, comprising:

a transfer mechanism, a connecting member, and an imaging mechanism sequentially arranged along a same optical axis from an image side; wherein the same optical axis of the transfer mechanism and the imaging mechanism is formed with a transfer lens sheath comprised by the transfer mechanism and an imaging lens sheath comprised by the imaging mechanism axially abutting against, in opposite directions, a radial outer wall and a radial inner wall of the connecting member, respectively; the connecting member being disposed at a transfer lens sheath object-side end, and the imaging lens sheath being disposed at a connecting member object-side end;

the transfer lens sheath is sleeved outwards with an inner lens sheath and an outer lens sheath sequentially, coaxially, and radially, and the outer lens sheath is axially separated from the inner lens sheath on an image side of the connecting member;

the outer lens sheath sleeves outer sides of the connecting member and the imaging lens sheath and at least partially and axially extends beyond an imaging lens sheath object-side end, and the outer lens sheath is radially separated from or connected to the connecting member, wherein the connecting member protrudes outwards radially to form an outer abutting portion for the transfer lens sheath to axially abut against, and the connecting member is concaved inwards radially to form a maintaining portion of the connecting member for the imaging lens sheath to axially abut against and partially extend into;

the same optical axis of the transfer lens sheath and the imaging lens sheath is formed with the transfer lens sheath and the imaging lens sheath axially abutting against, in opposite directions, the outer abutting portion and the maintaining portion, respectively;

wherein the outer lens sheath is radially connected to at least part of the outer abutting portion, wherein the outer lens sheath is fixedly connected to the at least part of the outer abutting portion, such that the outer lens sheath drives the connecting member to be axially separated from the transfer lens sheath;

wherein the transfer mechanism comprises three or more transfer lens sets, in an odder quantity, disposed at the transfer lens sheath at intervals of the same optical axis, and a plurality of first isolating rings axially abutted between adjacent two of the transfer lens sets;

the transfer lens set is symmetrically formed by two rod-shaped lens sets;

wherein the outer abutting portion forms a limiting end at least partially and axially extending into the transfer lens sheath, and the limiting end axially abuts against the rod-shaped lens set in a transfer lens sheath object-side end; and wherein the limiting end is circumferentially provided with at least one annular groove, and the annular groove is embedded with a filling layer preventing the transfer lens sheath from being axially separated from the connecting member.

2. The coaxial endoscopic optical system according to claim 1 wherein a gap is present between the outer lens sheath and the inner lens sheath for the outer lens sheath to be axially separated from the inner lens sheath.

3. The coaxial endoscopic optical system according to claim 1, wherein the filling layer is an adhesive medium or a sealing medium.

4. The coaxial endoscopic optical system according to claim 1, wherein the connecting member is constructed with a connecting channel arranged axially, the imaging lens sheath is partially accommodated in the connecting channel, and the connecting channel protrudes inwards radially to form the maintaining portion for the imaging lens sheath to axially abut against.

5. The coaxial endoscopic optical system according to claim 1, wherein the transfer lens sheath is in clearance or interference fitting with the inner lens sheath.

6. The coaxial endoscopic optical system according to claim 1, wherein the imaging mechanism comprises a first lens set with a positive focal power, a second lens set with a positive focal power, a third lens set with a positive focal power, and a fourth lens set with a positive focal power that are sequentially arranged from an object side along the same optical axis; wherein the first lens set comprises a second lens with a plane facing the object side, the second lens set comprises a fourth lens with a convex surface facing the object side and a fifth lens with a convex surface facing the image side that fit with each other, the third lens set comprises a sixth lens with a convex surface facing the object side and a concave surface facing the image side, and the fourth lens set comprises a seventh lens with a concave surface facing the object side and a convex surface facing the image side and an eighth lens with a convex surface facing the object side and a concave surface facing the image side, wherein a combined focal length $f_1$ of the first lens set and a conjugate distance T satisfy $$0.15 \leq f_1/T \leq 0.18,$$

a combined focal length $f_4$ of the fourth lens set and the combined focal length $f_1$ of the first lens set satisfy $$1.8 \leq f_4/f_1 \leq 2.2,$$

and a focal length $f_{41}$ of the seventh lens and a focal length $f_{42}$ of the eighth lens satisfy $$-1 \leq f_{42}/f_{41} \leq -0.8.$$

7. The coaxial endoscopic optical system according to claim 6, wherein the first lens set further comprises a third lens disposed on an image side of the second lens along the same optical axis; and a surface of the third lens facing the image side forms a convex surface.

8. The coaxial endoscopic optical system according to claim 6, wherein the first lens set further comprises a first lens disposed on an object side of the second lens along the same optical axis and having a plane facing the object side.

9. The coaxial endoscopic optical system according to claim 8, wherein the outer lens sheath axially extends beyond the imaging lens sheath object-side end to form a protective end, and the first lens is disposed at the protective end along the same optical axis.

10. The coaxial endoscopic optical system according to claim 1, wherein the coaxial endoscopic optical system further comprises:

a lens base configured at an outer lens sheath image-side end and an adapter base detachably connected to the lens base.

11. The coaxial endoscopic optical system according to claim 10, wherein the lens base is constructed with an accommodating channel accommodating at least part of the transfer lens sheath, and the accommodating channel forms radially inwards a step recess for a transfer lens sheath image-side end to axially abut against.

12. The coaxial endoscopic optical system according to claim 11, wherein the inner lens sheath axially penetrates through the adapter base and extends into the lens base, so as to abut against the step recess formed by the lens base, and the inner lens sheath is axially abutted between the lens base and the outer abutting portion.

13. An endoscopic imaging system, comprising a lens base with a dichroscope, a light source, and the coaxial endoscopic optical system according to claim 1; wherein the lens base receives light incident from the light source onto the dichroscope, and after reflection by the dichroscope, the coaxial endoscopic optical system captures the light reflected again by an object under test, and the reflected light penetrates through the dichroscope to be captured by the endoscopic imaging system.

14. A method of optically imaging a biological body tissue using the endoscopic imaging system according to claim 13, the method comprising:

causing light from the light source to be incident onto the dichroscope;

after reflection by the dichroscope, causing the light to pass through the coaxial endoscopic optical system to the biological body tissue; and capturing, by the endoscopic imaging system, light reflected by the biological body tissue after the reflected light penetrates through the dichroscope.

* * * * *